United States Patent
Laks et al.

(10) Patent No.: US 11,243,214 B2
(45) Date of Patent: Feb. 8, 2022

(54) BIOMARKER EXPRESSED IN PANCREATIC BETA CELLS USEFUL IN IMAGING OR TARGETING BETA CELLS

(71) Applicants: UNIVERSITÉ LIBRE DE BRUXELLES, Brussels (BE); VRIJE UNIVERSITEIT BRUSSEL, Brussels (BE)

(72) Inventors: Eizirik Decio Laks, Dilbeek (BE); Alexander Balhuizen, Brussels (BE); Nick Mark Devoogdt, Eppegem-Zemst (BE); Sam Marc Kris Aimé Massa, Hoeilaart (BE); Luc Bouwens, Dworp (BE); Iris Mathijs, Bambrugge (BE)

(73) Assignees: UNIVERSITÉ LIBRE DE BRUXELLES, Brussels (BE); VRIJE UNIVERSITES BRUSSEL, Brussels (BE)

( * ) Notice: Subject to any disclaimer, the term of this patent is extended or adjusted under 35 U.S.C. 154(b) by 405 days.

(21) Appl. No.: 16/092,212

(22) PCT Filed: Apr. 21, 2017

(86) PCT No.: PCT/EP2017/059459
§ 371 (c)(1),
(2) Date: Oct. 8, 2018

(87) PCT Pub. No.: WO2017/182603
PCT Pub. Date: Oct. 26, 2017

(65) Prior Publication Data
US 2019/0145987 A1 May 16, 2019

(30) Foreign Application Priority Data

Apr. 22, 2016 (EP) .................... 16166588

(51) Int. Cl.
*G01N 33/68* (2006.01)
*C07K 16/40* (2006.01)
*B01D 15/38* (2006.01)

(52) U.S. Cl.
CPC ..... *G01N 33/6893* (2013.01); *B01D 15/3809* (2013.01); *B01D 15/3823* (2013.01); *C07K 16/40* (2013.01); *C07K 2317/565* (2013.01); *C07K 2317/569* (2013.01); *C12N 2501/734* (2013.01); *G01N 2333/948* (2013.01); *G01N 2800/042* (2013.01)

(58) Field of Classification Search
CPC ............ B01D 15/3809; B01D 15/3823; C07K 16/40; C07K 2317/565; C07K 2317/569; C12N 2501/734; G01N 2333/948; G01N 2800/042; G01N 33/6893
See application file for complete search history.

(56) References Cited

U.S. PATENT DOCUMENTS

2010/0322850 A1  12/2010  Eizirik et al.

FOREIGN PATENT DOCUMENTS

WO  2010/096930 A1  9/2010
WO  2015/001113 A1  1/2015

OTHER PUBLICATIONS

Anonymous, Oct. 2015, "Anti-DPP6 Antibody Products", Biocompare, available at http://www.biocompare.com/pfu/110447/soids/3545/Antibodies/DPP6, 14 pages.
Brom et al., May 2010, "Development of Radiotracers for the Determination of the Beta-Cell Mass In Vivo", Current Pharmaceutical Design, vol. 16, No. 14, pp. 1561-1567.
Clark et al., Oct. 2008, "DPP6 localization in brain supports function as a Kv4 channel associated protein", Frontiers in Molecular Neuroscience, vol. 1, Article 8, pp. 1-11.
International Search Report and Written Opinion for International Patent Application No. PCT/EP2017/059459, 16 pages.
Nov. 1, 2018, International Preliminary Reporton Patentability for International Patent Application No. PCT/EP2017/059459, 11 pages.

*Primary Examiner* — Galina M. Yakovleva
(74) *Attorney, Agent, or Firm* — Lathrop GPM LLP; James H. Velema; Judith L. Stone-Hulslander

(57) ABSTRACT

The present invention is directed to the identification of a biomarker specifically located in the plasma membrane of pancreatic beta cells. Based on a set of specific features the biomarker is a unique candidate for imaging and targeting strategies to study the pancreatic beta cell mass in health and disease (T1D, T2D, pancreatic cancers, obesity, islet transplantation, beta cell regeneration).

17 Claims, 13 Drawing Sheets
Specification includes a Sequence Listing.

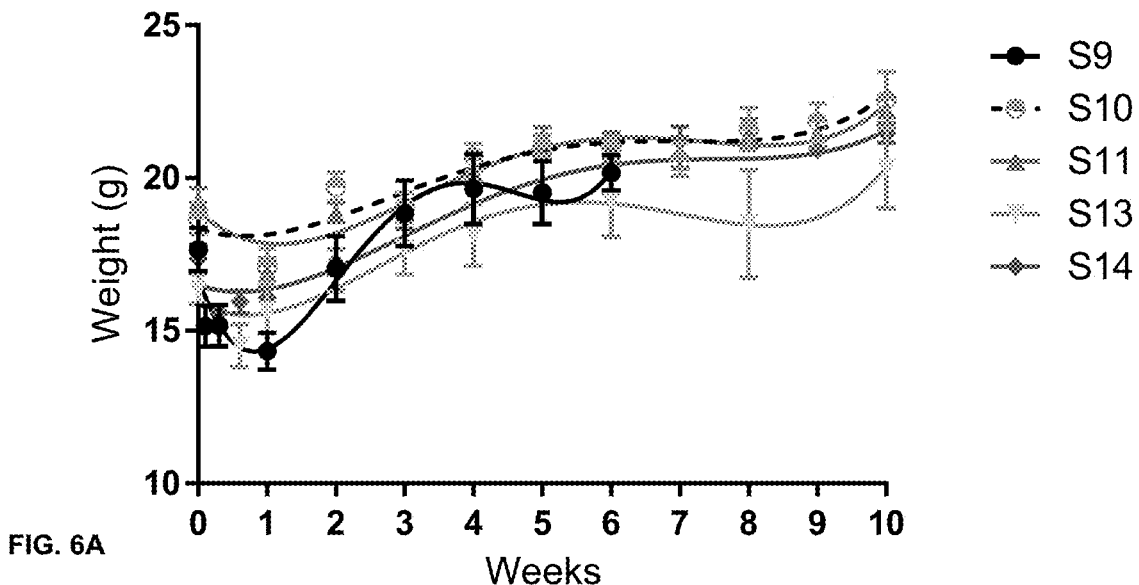
FIG. 6A
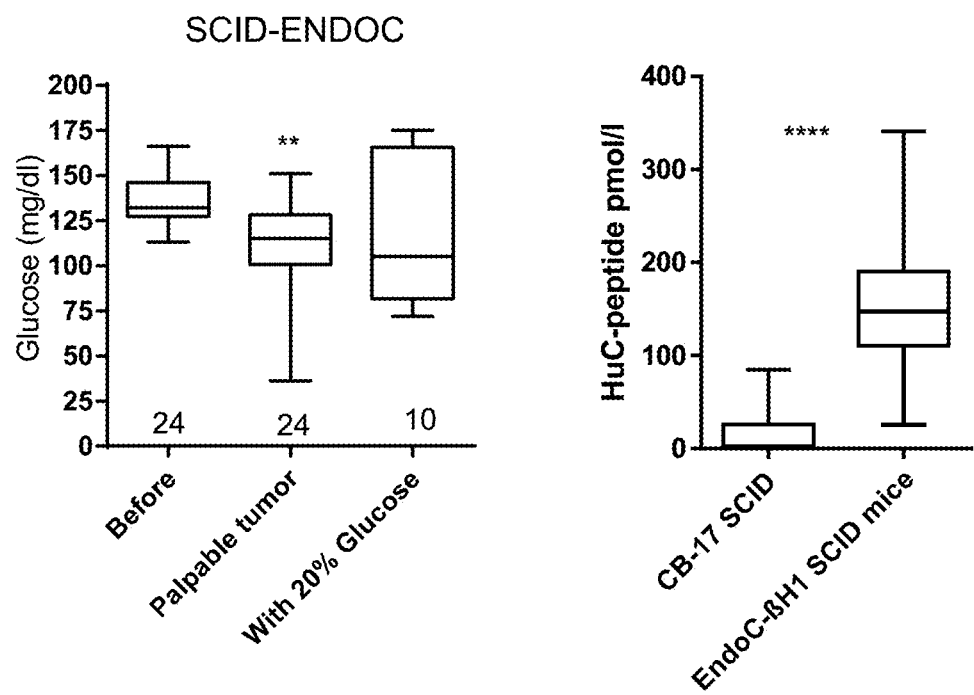
FIG. 6B
FIG. 6C

```
Clone   SEQ
        ID No
                  1           10          20          30          40          50          60
                  |-----------|-----------|-----------|-----------|-----------|-----------|
                  <-------FR1-IMGT------>  <-CDR1-IMGT>  <---FR2-IMGT---->  <CDR2IMGT>
4hD29   8         QVQLQESGG-GLVQPGGSLRLSCAAS GFTF----SSNY MTWVRQAPGKGPEWVSG INPD-GSST 70          80          90         100         115        120
                              |-----------|-----------|-----------|-----------|-----------|
                                                                          *1234554321*
                  <-------------FR3-IMGT--------------->  <----CDR3-IMGT----->  <FR4-IMGT->
                  YYADSVK-GRFTISRDNAKNTLYLQMNSLKSEDTALYKC ATGAAP----------RIPTTL RGQGTQVTVSS
```

FIG. 7

SEQUENCE LISTING

<160> NUMBER OF SEQ ID NOS: 11

<210> SEQ ID NO 1
<211> LENGTH: 801
<212> TYPE: PRT
<213> ORGANISM: Homo Sapiens

<400> SEQUENCE: 1

```
Met Lys Glu Lys Ala Met Ile Lys Thr Ala Lys Met Gln Gly Asn Val
1               5                   10                  15

Met Glu Leu Val Gly Ser Asn Pro Pro Gln Arg Asn Trp Lys Gly Ile
            20                  25                  30

Ala Ile Ala Leu Leu Val Ile Leu Val Ile Cys Ser Leu Ile Val Thr
        35                  40                  45

Ser Val Ile Leu Leu Thr Pro Ala Glu Asp Asn Ser Leu Ser Gln Lys
    50                  55                  60

Lys Lys Val Thr Val Glu Asp Leu Phe Ser Glu Asp Phe Lys Ile His
65                  70                  75                  80

Asp Pro Glu Ala Lys Trp Ile Ser Asp Thr Glu Phe Ile Tyr Arg Glu
                85                  90                  95

Gln Lys Gly Thr Val Arg Leu Trp Asn Val Glu Thr Asn Thr Ser Thr
            100                 105                 110

Val Leu Ile Glu Gly Lys Lys Ile Glu Ser Leu Arg Ala Ile Arg Tyr
        115                 120                 125

Glu Ile Ser Pro Asp Arg Glu Tyr Ala Leu Phe Ser Tyr Asn Val Glu
    130                 135                 140

Pro Ile Tyr Gln His Ser Tyr Thr Gly Tyr Tyr Val Leu Ser Lys Ile
145                 150                 155                 160

Pro His Gly Asp Pro Gln Ser Leu Asp Pro Pro Glu Val Ser Asn Ala
                165                 170                 175

Lys Leu Gln Tyr Ala Gly Trp Gly Pro Lys Gly Gln Gln Leu Ile Phe
            180                 185                 190

Ile Phe Glu Asn Asn Ile Tyr Tyr Cys Ala His Val Gly Lys Gln Ala
        195                 200                 205

Ile Arg Val Val Ser Thr Gly Lys Glu Gly Val Ile Tyr Asn Gly Leu
    210                 215                 220

Ser Asp Trp Leu Tyr Glu Glu Ile Leu Lys Thr His Ile Ala His
225                 230                 235                 240

Trp Trp Ser Pro Asp Gly Thr Arg Leu Ala Tyr Ala Ala Ile Asn Asp
                245                 250                 255

Ser Arg Val Pro Ile Met Glu Leu Pro Thr Tyr Thr Gly Ser Ile Tyr
            260                 265                 270

Pro Thr Val Lys Pro Tyr His Tyr Pro Lys Ala Gly Ser Glu Asn Pro
        275                 280                 285

Ser Ile Ser Leu His Val Ile Gly Leu Asn Gly Pro Thr His Asp Leu
    290                 295                 300

Glu Met Met Pro Pro Asp Asp Pro Arg Met Arg Glu Tyr Tyr Ile Thr
305                 310                 315                 320

Met Val Lys Trp Ala Thr Ser Thr Lys Val Ala Val Thr Trp Leu Asn
                325                 330                 335

Arg Ala Gln Asn Val Ser Ile Leu Thr Leu Cys Asp Ala Thr Thr Gly
            340                 345                 350

Val Cys Thr Lys Lys His Glu Asp Glu Ser Glu Ala Trp Leu His Arg
        355                 360                 365
```

-continued

```
Gln Asn Glu Glu Pro Val Phe Ser Lys Asp Gly Arg Lys Phe Phe
370                 375                 380

Ile Arg Ala Ile Pro Gln Gly Arg Gly Lys Phe Tyr His Ile Thr
385                 390                 395                 400

Val Ser Ser Gln Pro Asn Ser Ser Asn Asp Asn Ile Gln Ser Ile
            405                 410                 415

Thr Ser Gly Asp Trp Asp Val Thr Lys Ile Leu Ala Tyr Asp Glu Lys
            420                 425                 430

Gly Asn Lys Ile Tyr Phe Leu Ser Thr Glu Asp Leu Pro Arg Arg
            435                 440                 445

Gln Leu Tyr Ser Ala Asn Thr Val Gly Asn Phe Asn Arg Gln Cys Leu
450                 455                 460

Ser Cys Asp Leu Val Glu Asn Cys Thr Tyr Phe Ser Ala Ser Phe Ser
465                 470                 475                 480

His Ser Met Asp Phe Phe Leu Leu Lys Cys Glu Gly Pro Gly Val Pro
                485                 490                 495

Met Val Thr Val His Asn Thr Thr Asp Lys Lys Met Phe Asp Leu
            500                 505                 510

Glu Thr Asn Glu His Val Lys Lys Ala Ile Asn Asp Arg Gln Met Pro
515                 520                 525

Lys Val Glu Tyr Arg Asp Ile Glu Ile Asp Tyr Asn Leu Pro Met
530                 535                 540

Gln Ile Leu Lys Pro Ala Thr Phe Thr Asp Thr Thr His Tyr Pro Leu
545                 550                 555                 560

Leu Leu Val Val Asp Gly Thr Pro Gly Ser Gln Ser Val Ala Glu Lys
                565                 570                 575

Phe Glu Val Ser Trp Glu Thr Val Met Val Ser Ser His Gly Ala Val
                580                 585                 590

Val Val Lys Cys Asp Gly Arg Gly Ser Gly Phe Gln Gly Thr Lys Leu
        595                 600                 605

Leu His Glu Val Arg Arg Arg Leu Gly Leu Leu Glu Glu Lys Asp Gln
    610                 615                 620

Met Glu Ala Val Arg Thr Met Leu Lys Glu Gln Tyr Ile Asp Arg Thr
625                 630                 635                 640

Arg Val Ala Val Phe Gly Lys Asp Tyr Gly Gly Tyr Leu Ser Thr Tyr
                645                 650                 655

Ile Leu Pro Ala Lys Gly Glu Asn Gln Gly Gln Thr Phe Thr Cys Gly
                660                 665                 670

Ser Ala Leu Ser Pro Ile Thr Asp Phe Lys Leu Tyr Ala Ser Ala Phe
            675                 680                 685

Ser Glu Arg Tyr Leu Gly Leu His Gly Leu Asp Asn Arg Ala Tyr Glu
    690                 695                 700

Met Thr Lys Val Ala His Arg Val Ser Ala Leu Glu Glu Gln Gln Phe
705                 710                 715                 720

Leu Ile Ile His Pro Thr Ala Asp Glu Lys Ile His Phe Gln His Thr
                725                 730                 735

Ala Glu Leu Ile Thr Gln Leu Ile Arg Gly Lys Ala Asn Tyr Ser Leu
            740                 745                 750

Gln Ile Tyr Pro Asp Glu Ser His Tyr Phe Thr Ser Ser Ser Leu Lys
    755                 760                 765

Gln His Leu Tyr Arg Ser Ile Ile Asn Phe Phe Val Glu Cys Phe Arg
770                 775                 780

Ile Gln Asp Lys Leu Leu Thr Val Thr Ala Lys Glu Asp Glu Glu Glu
```

```
                785                 790                 795                 800
Asp

<210> SEQ ID NO 2
<211> LENGTH: 801
<212> TYPE: PRT
<213> ORGANISM: Homo Sapiens

<400> SEQUENCE: 2

Met Lys Glu Lys Ala Met Ile Lys Thr Ala Lys Met Gln Gly Asn Val
1               5                   10                  15

Met Glu Leu Val Gly Ser Asn Pro Pro Gln Arg Asn Trp Lys Gly Ile
            20                  25                  30

Ala Ile Ala Leu Leu Val Ile Leu Val Ile Cys Ser Leu Ile Val Thr
        35                  40                  45

Ser Val Ile Leu Leu Thr Pro Ala Glu Asp Thr Ser Leu Ser Gln Lys
    50                  55                  60

Lys Lys Val Thr Val Glu Asp Leu Phe Ser Glu Asp Phe Lys Ile His
65                  70                  75                  80

Asp Pro Glu Ala Lys Trp Ile Ser Asn Lys Glu Phe Ile Tyr Arg Glu
                85                  90                  95

Arg Lys Gly Ser Val Ile Leu Arg Asn Val Glu Thr Asn Asn Ser Thr
            100                 105                 110

Val Leu Ile Glu Gly Lys Lys Ile Glu Ser Leu Arg Ala Ile Arg Tyr
        115                 120                 125

Glu Ile Ser Pro Asp Lys Glu Tyr Val Leu Phe Ser Tyr Asn Val Glu
130                 135                 140

Pro Val Tyr Gln His Ser His Thr Gly Tyr Tyr Val Leu Ser Lys Ile
145                 150                 155                 160

Pro His Gly Asp Pro Gln Ser Leu Asp Pro Pro Glu Val Ser Asn Ala
                165                 170                 175

Lys Leu Gln Tyr Ala Gly Trp Gly Pro Lys Gly Gln Gln Leu Ile Phe
            180                 185                 190

Ile Phe Glu Asn Asn Ile Tyr Tyr Cys Ala His Val Gly Lys Gln Ala
        195                 200                 205

Ile Arg Val Val Ser Thr Gly Lys Glu Gly Val Ile Tyr Asn Gly Leu
210                 215                 220

Ser Asp Trp Leu Tyr Glu Glu Glu Ile Leu Lys Ser His Ile Ala His
225                 230                 235                 240

Trp Trp Ser Pro Asp Gly Thr Arg Leu Ala Tyr Ala Thr Ile Asn Asp
                245                 250                 255

Ser Arg Val Pro Leu Met Glu Leu Pro Thr Tyr Thr Gly Ser Val Tyr
            260                 265                 270

Pro Thr Val Lys Pro Tyr His Tyr Pro Lys Ala Gly Ser Glu Asn Pro
        275                 280                 285

Ser Ile Ser Leu His Val Ile Gly Leu Asn Gly Pro Thr His Asp Leu
290                 295                 300

Glu Met Met Pro Pro Asp Asp Pro Arg Met Arg Glu Tyr Tyr Ile Thr
305                 310                 315                 320

Met Val Lys Trp Ala Thr Ser Thr Lys Val Ala Val Thr Trp Leu Asn
                325                 330                 335

Arg Ala Gln Asn Val Ser Ile Leu Thr Leu Cys Asp Ala Thr Thr Gly
            340                 345                 350

Val Cys Thr Lys Lys His Glu Asp Glu Ser Glu Ala Trp Leu His Arg
```

```
                355                 360                 365
Gln Asn Glu Glu Pro Val Phe Ser Lys Asp Gly Arg Lys Phe Phe
    370                 375                 380
Val Arg Ala Ile Pro Gln Gly Gly Arg Gly Lys Phe Tyr His Ile Thr
385                 390                 395                 400
Val Ser Ser Ser Gln Pro Asn Ser Ser Asn Asp Asn Ile Gln Ser Ile
                405                 410                 415
Thr Ser Gly Asp Trp Asp Val Thr Lys Ile Leu Ser Tyr Asp Glu Lys
                420                 425                 430
Arg Asn Lys Ile Tyr Phe Leu Ser Thr Glu Asp Leu Pro Arg Arg
                435                 440                 445
His Leu Tyr Ser Ala Asn Thr Val Asp Asp Phe Asn Arg Gln Cys Leu
    450                 455                 460
Ser Cys Asp Leu Val Glu Asn Cys Thr Tyr Val Ser Ala Ser Phe Ser
465                 470                 475                 480
His Asn Met Asp Phe Phe Leu Leu Lys Cys Glu Gly Pro Gly Val Pro
                485                 490                 495
Thr Val Thr Val His Asn Thr Thr Asp Lys Arg Arg Met Phe Asp Leu
                500                 505                 510
Glu Ala Asn Glu Glu Val Gln Lys Ala Ile Asn Asp Arg Gln Met Pro
    515                 520                 525
Lys Ile Glu Tyr Arg Lys Ile Glu Val Glu Asp Tyr Ser Leu Pro Met
530                 535                 540
Gln Ile Leu Lys Pro Ala Thr Phe Thr Asp Thr Ala His Tyr Pro Leu
545                 550                 555                 560
Leu Leu Val Val Asp Gly Thr Pro Gly Ser Gln Ser Val Thr Glu Arg
                565                 570                 575
Phe Glu Val Thr Trp Glu Thr Val Leu Val Ser Ser His Gly Ala Val
                580                 585                 590
Val Val Lys Cys Asp Gly Arg Gly Ser Gly Phe Gln Gly Thr Lys Leu
    595                 600                 605
Leu Gln Glu Val Arg Arg Arg Leu Gly Phe Leu Glu Glu Lys Asp Gln
    610                 615                 620
Met Glu Ala Val Arg Thr Met Leu Lys Glu Gln Tyr Ile Asp Lys Thr
625                 630                 635                 640
Arg Val Ala Val Phe Gly Lys Asp Tyr Gly Gly Tyr Leu Ser Thr Tyr
                645                 650                 655
Ile Leu Pro Ala Lys Gly Glu Asn Gln Gly Gln Thr Phe Thr Cys Gly
                660                 665                 670
Ser Ala Leu Ser Pro Ile Thr Asp Phe Lys Leu Tyr Ala Ser Ala Phe
    675                 680                 685
Ser Glu Arg Tyr Leu Gly Leu His Gly Leu Asp Asn Arg Ala Tyr Glu
    690                 695                 700
Met Thr Lys Leu Ala His Arg Val Ser Ala Leu Glu Asp Gln Gln Phe
705                 710                 715                 720
Leu Ile Ile His Ala Thr Ala Asp Glu Lys Ile His Phe Gln His Thr
                725                 730                 735
Ala Glu Leu Ile Thr Gln Leu Ile Lys Gly Lys Ala Asn Tyr Ser Leu
                740                 745                 750
Gln Ile Tyr Pro Asp Glu Ser His Tyr Phe His Ser Val Ala Leu Lys
    755                 760                 765
Gln His Leu Ser Arg Ser Ile Ile Gly Phe Phe Val Glu Cys Phe Arg
    770                 775                 780
```

```
Val Gln Asp Lys Leu Pro Thr Ala Thr Ala Lys Glu Glu Glu Glu
785                 790                 795                 800

Asp

<210> SEQ ID NO 3
<211> LENGTH: 749
<212> TYPE: PRT
<213> ORGANISM: Homo Sapiens

<400> SEQUENCE: 3

Leu Thr Pro Ala Glu Asp Asn Ser Leu Ser Gln Lys Lys Val Thr
1               5                   10                  15

Val Glu Asp Leu Phe Ser Glu Asp Phe Lys Ile His Asp Pro Glu Ala
            20                  25                  30

Lys Trp Ile Ser Asp Thr Glu Phe Ile Tyr Arg Glu Gln Lys Gly Thr
                35                  40                  45

Val Arg Leu Trp Asn Val Glu Thr Asn Thr Ser Thr Val Leu Ile Glu
50                  55                  60

Gly Lys Lys Ile Glu Ser Leu Arg Ala Ile Arg Tyr Glu Ile Ser Pro
65                  70                  75                  80

Asp Arg Glu Tyr Ala Leu Phe Ser Tyr Asn Val Glu Pro Ile Tyr Gln
                85                  90                  95

His Ser Tyr Thr Gly Tyr Tyr Val Leu Ser Lys Ile Pro His Gly Asp
            100                 105                 110

Pro Gln Ser Leu Asp Pro Pro Glu Val Ser Asn Ala Lys Leu Gln Tyr
        115                 120                 125

Ala Gly Trp Gly Pro Lys Gly Gln Gln Leu Ile Phe Ile Phe Glu Asn
130                 135                 140

Asn Ile Tyr Tyr Cys Ala His Val Gly Lys Gln Ala Ile Arg Val Val
145                 150                 155                 160

Ser Thr Gly Lys Glu Gly Val Ile Tyr Asn Gly Leu Ser Asp Trp Leu
                165                 170                 175

Tyr Glu Glu Glu Ile Leu Lys Thr His Ile Ala His Trp Trp Ser Pro
            180                 185                 190

Asp Gly Thr Arg Leu Ala Tyr Ala Ala Ile Asn Asp Ser Arg Val Pro
        195                 200                 205

Ile Met Glu Leu Pro Thr Tyr Thr Gly Ser Ile Tyr Pro Thr Val Lys
210                 215                 220

Pro Tyr His Tyr Pro Lys Ala Gly Ser Glu Asn Pro Ser Ile Ser Leu
225                 230                 235                 240

His Val Ile Gly Leu Asn Gly Pro Thr His Asp Leu Glu Met Met Pro
                245                 250                 255

Pro Asp Asp Pro Arg Met Arg Glu Tyr Tyr Ile Thr Met Val Lys Trp
            260                 265                 270

Ala Thr Ser Thr Lys Val Ala Val Thr Trp Leu Asn Arg Ala Gln Asn
        275                 280                 285

Val Ser Ile Leu Thr Leu Cys Asp Ala Thr Thr Gly Val Cys Thr Lys
290                 295                 300

Lys His Glu Asp Glu Ser Glu Ala Trp Leu His Arg Gln Asn Glu Glu
305                 310                 315                 320

Pro Val Phe Ser Lys Asp Gly Arg Lys Phe Phe Ile Arg Ala Ile
                325                 330                 335

Pro Gln Gly Gly Arg Gly Lys Phe Tyr His Ile Thr Val Ser Ser Ser
            340                 345                 350
```

-continued

```
Gln Pro Asn Ser Ser Asn Asp Asn Ile Gln Ser Ile Thr Ser Gly Asp
        355                 360                 365

Trp Asp Val Thr Lys Ile Leu Ala Tyr Asp Glu Lys Gly Asn Lys Ile
370                 375                 380

Tyr Phe Leu Ser Thr Glu Asp Leu Pro Arg Arg Gln Leu Tyr Ser
385                 390                 395                 400

Ala Asn Thr Val Gly Asn Phe Asn Arg Gln Cys Leu Ser Cys Asp Leu
                405                 410                 415

Val Glu Asn Cys Thr Tyr Phe Ser Ala Ser Phe Ser His Ser Met Asp
                420                 425                 430

Phe Phe Leu Leu Lys Cys Glu Gly Pro Gly Val Pro Met Val Thr Val
                435                 440                 445

His Asn Thr Thr Asp Lys Lys Lys Met Phe Asp Leu Glu Thr Asn Glu
        450                 455                 460

His Val Lys Lys Ala Ile Asn Asp Arg Gln Met Pro Lys Val Glu Tyr
465                 470                 475                 480

Arg Asp Ile Glu Ile Asp Asp Tyr Asn Leu Pro Met Gln Ile Leu Lys
                485                 490                 495

Pro Ala Thr Phe Thr Asp Thr Thr His Tyr Pro Leu Leu Leu Val Val
                500                 505                 510

Asp Gly Thr Pro Gly Ser Gln Ser Val Ala Glu Lys Phe Glu Val Ser
                515                 520                 525

Trp Glu Thr Val Met Val Ser Ser His Gly Ala Val Val Lys Cys
530                 535                 540

Asp Gly Arg Gly Ser Gly Phe Gln Gly Thr Lys Leu Leu His Glu Val
545                 550                 555                 560

Arg Arg Arg Leu Gly Leu Leu Glu Glu Lys Asp Gln Met Glu Ala Val
                565                 570                 575

Arg Thr Met Leu Lys Glu Gln Tyr Ile Asp Arg Thr Arg Val Ala Val
                580                 585                 590

Phe Gly Lys Asp Tyr Gly Gly Tyr Leu Ser Thr Tyr Ile Leu Pro Ala
                595                 600                 605

Lys Gly Glu Asn Gln Gly Gln Thr Phe Thr Cys Gly Ser Ala Leu Ser
610                 615                 620

Pro Ile Thr Asp Phe Lys Leu Tyr Ala Ser Ala Phe Ser Glu Arg Tyr
625                 630                 635                 640

Leu Gly Leu His Gly Leu Asp Asn Arg Ala Tyr Glu Met Thr Lys Val
                645                 650                 655

Ala His Arg Val Ser Ala Leu Glu Glu Gln Gln Phe Leu Ile Ile His
                660                 665                 670

Pro Thr Ala Asp Glu Lys Ile His Phe Gln His Thr Ala Glu Leu Ile
                675                 680                 685

Thr Gln Leu Ile Arg Gly Lys Ala Asn Tyr Ser Leu Gln Ile Tyr Pro
        690                 695                 700

Asp Glu Ser His Tyr Phe Thr Ser Ser Ser Leu Lys Gln His Leu Tyr
705                 710                 715                 720

Arg Ser Ile Ile Asn Phe Phe Val Glu Cys Phe Arg Ile Gln Asp Lys
                725                 730                 735

Leu Leu Thr Val Thr Ala Lys Glu Asp Glu Glu Asp
                740                 745

<210> SEQ ID NO 4
<211> LENGTH: 23
```

```
<212> TYPE: DNA
<213> ORGANISM: Artificial
<220> FEATURE:
<223> OTHER INFORMATION: Primer

<400> SEQUENCE: 4
acagtgagac tgtggaatgt tga                                              23

<210> SEQ ID NO 5
<211> LENGTH: 23
<212> TYPE: DNA
<213> ORGANISM: Artificial
<220> FEATURE:
<223> OTHER INFORMATION: Primer

<400> SEQUENCE: 5
gaggatcccc atgaggaatt ttg                                              23

<210> SEQ ID NO 6
<211> LENGTH: 25
<212> TYPE: DNA
<213> ORGANISM: Artificial
<220> FEATURE:
<223> OTHER INFORMATION: Primer

<400> SEQUENCE: 6
gcctggagaa acctgccaag tatga                                            25

<210> SEQ ID NO 7
<211> LENGTH: 22
<212> TYPE: DNA
<213> ORGANISM: Artificial
<220> FEATURE:
<223> OTHER INFORMATION: Primer

<400> SEQUENCE: 7
aacctggtcc tcagtgtagc cc                                               22

<210> SEQ ID NO 8
<211> LENGTH: 119
<212> TYPE: PRT
<213> ORGANISM: Artificial
<220> FEATURE:
<223> OTHER INFORMATION: Nanobody

<400> SEQUENCE: 8
```

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Thr Trp Val Arg Gln Ala Pro Gly Lys Gly Pro Glu Trp Val
        35                  40                  45

Ser Gly Ile Asn Pro Asp Gly Ser Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Leu Tyr Lys Cys
                85                  90                  95

Ala Thr Gly Ala Ala Pro Arg Ile Pro Thr Thr Leu Arg Gly Gln Gly
            100                 105                 110

Thr Gln Val Thr Val Ser Ser
        115

```
<210> SEQ ID NO 9
<211> LENGTH: 8
<212> TYPE: PRT
<213> ORGANISM: Artificial
<220> FEATURE:
<223> OTHER INFORMATION: CDR region of nanobody

<400> SEQUENCE: 9

Gly Phe Thr Phe Ser Ser Asn Tyr
1               5

<210> SEQ ID NO 10
<211> LENGTH: 8
<212> TYPE: PRT
<213> ORGANISM: Artificial
<220> FEATURE:
<223> OTHER INFORMATION: CDR region of nanobody

<400> SEQUENCE: 10

Ile Asn Pro Asp Gly Ser Ser Thr
1               5

<210> SEQ ID NO 11
<211> LENGTH: 12
<212> TYPE: PRT
<213> ORGANISM: Artificial
<220> FEATURE:
<223> OTHER INFORMATION: CDR region of nanobody

<400> SEQUENCE: 11

Ala Thr Gly Ala Ala Pro Arg Ile Pro Thr Thr Leu
1               5                   10
```

BIOMARKER EXPRESSED IN PANCREATIC BETA CELLS USEFUL IN IMAGING OR TARGETING BETA CELLS

RELATED APPLICATIONS

This application is a 35 U.S.C. § 371 filing of International Patent Application No. PCT/EP2017/059459, filed Apr. 21, 2017, which claims the benefit of priority to European Patent Application No. 16166588.0, filed Apr. 22, 2016. The entire contents of these applications are incorporated herein by reference for all purposes.

FIELD OF THE INVENTION

The present invention is directed to the medical field, in particular to the imaging and quantification of pancreatic beta cell mass, targeting or visualization of pancreatic beta cells for pathology and/or follow up of diabetic disorders, follow up of islet transplantation and to purification strategies of pancreatic beta cells.

BACKGROUND OF THE INVENTION

Diabetes is caused by insufficient production of insulin, the key hormone responsible for controlling blood glucose levels. Insulin is produced by beta cells located in the islets of Langerhans, clusters of endocrine cells diffusely distributed throughout the pancreas. Medical textbooks define type 1 diabetes (T1D) as a result of a progressive and eventually complete loss of beta cell mass following autoimmune destruction, whereas type 2 diabetes (T2D) is described as being caused by insulin resistance in peripheral tissues, that is not adequately compensated for by the pancreatic beta cells, that is more prevalent in obese patients, leading to progressive beta cell failure (and eventually death), at least in part due to chronic metabolic stress. The standard treatment for T1D has been multiple daily injections of insulin to control blood glucose levels in the patient. In T2D, however, (initial) therapy is lifestyle changes (weight loss and exercise), often in combination with drugs stimulating release of endogenous insulin and/or increase peripheral insulin sensitivity, with addition of insulin if needed. Emerging and exciting evidence, however, suggests that the dogma that in longstanding T1D all beta cells are destroyed and the pancreas cannot produce insulin, is probably wrong for many of the patients. As initially suggested by work performed in non-obese diabetic (NOD) mice (Strandell, E. et al. (1990) J. Clin. Invest. 85, 1944-1950), and in islets isolated from T1D patients (Marchetti, P. et al. (2000) Diabetes Care 23, 701-703), a population of functionally suppressed but still alive beta cells remains. These cells are able to produce and secrete small amounts of insulin, as shown by measuring C-peptide, and most importantly, they may survive for decades after the diagnosis of T1D (Keenan, H. A. et al. (2010) Diabetes 59, 2846-2853; Oram, R. A. et al. (2014) Diabetologia 57, 187-191; Couri, C. E. et al. (2009) JAMA 301, 1573-1579). These new findings require a big conceptual change in how we understand T1D and, although they have been initially perceived with disbelief by many scientists (Faustmann, D. L. (2014) Diabetologia 57, 1-3), they open new avenues towards creating new approaches to tackle an old problem.

Currently, the natural history of beta cell loss in T1D and T2D and the relationship between (anatomical) beta cell mass and function in the course of diabetes is not clear. For T2D patients, for example, it has been demonstrated that beta cell function may deteriorate, whereas beta cell mass is preserved. Another level of complication is that there are marked (>fivefold) interindividual differences in beta cell mass (Meier, J. J. et al. (2009) Diabetes 58, 1595-1603; Rahier, J. et al. (2008) Diabetes Obes. Metab. 10 (Suppl. 4), 32-42), with a large overlap between non-diabetic individuals and patients with impaired glucose tolerance/overt diabetes (Ritzel, R. A. et al. (2006) Diabetes Care 29, 717-718). Individual T2D patients have a diverse pathophysiology and differ in the progression of the disease. It is presently not possible to predict individually which T2D patients will eventually need insulin therapy. T1D patients may have remaining beta cells decades after the onset of disease, and we do not know how these residual beta cells influence the course of the disease: do they help to stabilize blood glucose levels, reduce the rate of diabetes complications, or prevent hypoglycemia? It is crucial to underline that clinical diabetes depends not only on the absolute amount of beta cells but also on the function of the individual beta cells. Patients with diabetes or impaired glucose tolerance tend to have a lower beta cell mass, but beta cell mass by itself does not necessarily predict the glucose tolerance of individual patients. Knowledge about the beta cell mass in relation to its function may help to predict individually who will develop diabetes and who will respond or not to particular therapies. So far, all human studies to determine beta cell mass have been carried out on pancreatic specimens obtained by pancreatectomy or from autopsies, whereas beta cell function is assessed non-invasively by glucose tolerance testing or clamping. A challenge for histological determination of beta cell mass in tissue specimens is that beta cells may be viable but non-functional (Coppieters, K. T. et al. (2012) J. Exp. Med. 209, 51-60), in other words degranulated and/or not releasing insulin, such that they may be missed when anti-insulin staining is used for immunohistochemical determination of beta cell mass—meaning that the true beta cell mass is underestimated (Marselli, L. et al. (2014) Diabetologia 57, 362-365). In addition, beta cells may be detected as insulin-positive even though they may be unable to release the hormone in vivo. It is therefore clear that non-invasive methods for determining beta cell mass are warranted, such as non-invasive imaging methods or blood biomarkers. These methods, analyzed in parallel with C-peptide release, would ideally allow the detection of both functional beta cells (beta cell mass and stimulated C-peptide are in agreement) and non-functional beta cells (beta cells are present, but there is no or very low stimulated C-peptide release). This would enable independence from tissue specimens, with their inherent limitations, and would open a window of opportunity for cross-sectional as well as longitudinal clinical studies in large numbers of patients. Beta cell mass and function are not equivalent—determination of individual beta cell function and mass may therefore be a cornerstone of future individualized treatment and prevention of diabetes. Knowing the remaining beta cell mass in diabetic patients or in individuals at risk of developing the disease, and linking this information to the evaluation of beta cell function in longitudinal studies, would massively improve our understanding of the pathophysiology and natural history of diabetes. This knowledge is also expected to enable the development of novel treatment and prevention strategies. So far, few studies have compared the effect of T2D drug treatments on residual beta cell function, often using poor functional measures such as homeostasis model assessment (HOMA). Imaging beta cell mass as compared to function will enable comparative studies between glucose-lowering drugs. It will allow individualization of patient treatment, for example by identifying those individuals with T2D that would benefit from therapies relying on the presence of viable, insulin-secreting beta cells, such as sulfonylureas or glucagon-like peptide-1 (GLP-1) analogs, whereas others with limited beta cell reserve may directly change to insulin replacement. In the case of T1D, the presence of a substantial reserve of non-functional beta cells may indicate the use of anti-inflammatory agents (e.g., cytokine blockers) in parallel to insulin therapy, with the hope of restoring some endogenous insulin release. As stated above, knowing the functional level of the beta cells, in relation to the beta cell mass of an individual might help us to predict better the course of the disease and to define the best approaches individually to prevent, reverse, and treat diabetes.

Currently, attempts at in vivo visualization of beta cells in humans rely on radiolabeled tracer molecules that bind to beta cells with high specificity. These radiotracers can be detected in the picomolar range by positron emission tomography (PET) and single photon emission computed tomography (SPECT). Although the spatial resolution of both types of scanners does not allow single islets to be resolved, the signal detected in the pancreas is highly specific when the radiotracers specifically bind to beta cells (Andralojc, K. et al. (2012) Diabetologia 55, 1247-1257). Currently, three radiotracers are undergoing early clinical evaluation: $^{18}$F-dihydro-tetrabenazine (DTBZ) for imaging of vesicular monoamine transporter 2 (VMAT2), $^{11}$C-hydroxytryptophane (HTP) as a marker for the serotonergic system, and $^{111}$In- and $^{68}$Ga-labeled exendin targeting the glucagon-like peptide-1 (GLP-1) receptor. Although 30% of the DTBZ signal seems to originate from beta cells (the remaining 70% originates from other endocrine cells) (Freeby, M. et al. (2012) Islets 4, 393-397), and HTP is a marker for the complete endocrine pancreas (i.e., all cells in the islets of Langerhans), exendin is suggested to be specific for beta cells (Brom, M. et al. (2014) Diabetologia dx.doi.org/10.1007/s00125-014-3166-3). Of concern, however, beta cell imaging based on labeled exendin shows only a 50% decrease in beta cell mass in patients with >15-20 years of T1D, a stage of the disease where most patients have lost >95% of their beta cells, suggesting lack of sufficient specificity. Discovery of novel beta cell biomarkers, such as for instance specific splice variants present in beta cells only, may improve the potential for radiotracer-based imaging in the future. Although the clinically available radiotracers give us different information, it is intriguing that all three of them show a considerable overlap of the signal detected in the pancreas between healthy individuals and T1D patients, indicating the presence of residual beta cell mass in T1D patients and large interindividual variations among healthy individuals. These results are in line with the histology-based findings discussed above, suggesting that currently available imaging methods deliver information about pancreatic beta cell mass. This information, however, is not yet sufficient for accurate follow up of beta cell mass in diabetic patients.

Beta cells constitute 1-3% of the pancreatic mass and are scattered throughout the pancreas in the tiny islets of Langerhans (100-300 micrometer in diameter). The disperse localization of the cells (unlike tumor cells) makes imaging challenging. An additional level of complexity is that, to determine the differences in anatomical beta cell mass between diabetic subjects, all intact islets remaining in later stages of diabetes need to be detectable, thus detection methods must be exquisitely sensitive. Single islets cannot yet be spatially resolved non-invasively in vivo in humans.

A highly sensitive method is thus necessary to permit easy quantification of tracer uptake in the endocrine pancreas, without necessarily requiring resolution of single beta cells/islets. Therefore, approaches for clinical beta cell imaging should primarily rely on chemical resolution with high sensitivity (i.e., visualization of beta cells based on high specificity and biochemical/metabolic characteristics of a tracer molecule) by using tracers for positron emission tomography (PET) or single photon emission computed tomography (SPECT), techniques characterized by a very high sensitivity.

Consequently, there is a need for specific and reliable biomarkers for the identification and visualization of beta cells of pancreatic islets of Langerhans, which allow reliable beta cell mass quantification. One of the aims of the present invention is to provide such markers.

SUMMARY OF THE INVENTION

The present invention is directed to a biomarker that is specifically expressed on beta-cells. This biomarker is a unique candidate for imaging and targeting strategies to study the pancreatic beta cell mass in health and disease (type 1 diabetes mellitus (T1D), type 2 diabetes mellitus (T2D), hyperinsulinemia, obesity, neuroendocrine tumors, occurrence of insulinoma or islet transplantation). The biomarker is preferentially expressed in beta cells and can be used for beta cell targeting and non-invasive in vivo imaging. The use of targeting strategies against these biomarkers will allow early identification of variation in beta cell mass and the follow-up of therapies for diabetes, including islet transplantation, attempts at beta cell regeneration etc.

Imaging/targeting strategies using labeled antibodies, aptamers, interacting proteins, peptides or ligands directed against or specifically binding to these biomarkers will allow beta cell specific labeling and visualisation, beta cell mass quantification, evaluate the progression of diabetes, and will lead to earlier prediction of pancreatic disease state, allow earlier intervention and higher chance to cure or halt diabetes, and enable the follow up of beta cell mass following islet transplantation.

The biomarker of the invention can also be a potential target for autoimmunity in T1D, as is the case of other abundant beta cell surface proteins, and may thus be a target for auto-antibodies or T-cells. Detection of these auto-antibodies and T-cells may allow prediction of T1D.

Another application of the biomarker as disclosed herein will be the follow-up of beta cell mass in patients with type 1 and type 2 diabetes and following islet transplantation. Beta cell imaging will be also useful as a surrogate marker for clinical trials of new therapies aiming to prevent beta cell mass loss in diabetes or to restore beta cell mass by regeneration. The biomarkers could also be targeted to deliver agents to stop inflammation in the case of T1D or transplantation. Finally, measurement of the biomarker (RNA or protein) in the circulation may provide indication of ongoing beta cell death in diabetes.

The invention provides the following aspects:
1. Use of the DPP6-K splice variant (also referred to herein as "DPP6-K") as a biomarker for detecting pancreatic beta cells. Preferably said use in in vitro and/or in vivo.
2. The use according to aspect 1, wherein said DPP6-K splice variant is used for visualising or measuring pancreatic beta cell mass. Preferably said use in in vitro and/or in vivo.
3. The use according to aspect 1, wherein said DPP6-K splice variant is used as a circulation marker for detecting damaged beta-cells and/or beta cell debris in a blood, plasma, serum, or urine sample of a subject. Preferably said use in in vitro and/or in vivo.
4. The use according to any one of aspects 1 to 3, wherein said DPP6-K splice variant is defined by the sequence of SEQ ID NO: 1.
5. A method for detecting and/or visualising pancreatic beta-cells comprising the steps of:
   a) labelling beta cells in a sample of a subject based on the presence of the DPP6-K splice variant,
   b) detecting or visualising the labelled beta cells. Preferably said method is performed in in vitro and/or in vivo.
6. A method for measuring pancreatic beta-cell mass comprising the steps of:
   a) detecting or visualizing the beta cells in a sample of a subject using the method according to aspect 5, and
   b) quantifying the amount of labelled beta cells.
7. Use of a binding molecule specifically binding to the extracellular domain of DPP6-K, in the preparation of a composition for the in vitro and/or in-vivo visualisation of pancreatic beta cells; Binding molecule specifically binding to DPP6-K, for use in the in-vivo visualisation of pancreatic beta cells; or Use of a binding molecule specifically binding to DPP6-K, for the in-vitro visualisation of pancreatic beta cells.
8. Use of a binding molecule specifically binding to DPP6-K, especially to the extracellular domain of DPP6-K, in the preparation of a composition for the in vitro and/or in-vivo diagnosis of pancreatic beta-cell related disorders; Binding molecule specifically binding to DPP6-K, for use in the in-vivo diagnosis of pancreatic beta-cell related disorders; or Use of a binding molecule specifically binding to DPP6-K, for the in-vitro diagnosis of pancreatic beta-cell related disorders.
9. The use according to aspect 8, wherein said pancreatic beta-cell related disorder is type 1 diabetes mellitus, type 2 diabetes mellitus, hyperinsulinemia, obesity, neuroendocrine tumors or occurrence of insulinoma, preferably type-1-diabetes mellitus.
10. A method of in vivo diagnosing a beta-cell-related disorder encompassing the following steps:
    a) introducing a labelled molecule, specifically binding to the extracellular domain of DPP6-K, into a subject,
    b) visualizing the labelled molecule specifically located to the beta cell population in the pancreas in vivo,
    c) quantifying the beta cells mass in said subject,
    d) comparing the beta cell mass data obtained in step c) with the beta cell mass of a healthy subject, or of a previous analysis of the same subject.
    e) diagnosing the subject as having diabetes or being at risk of having diabetes when the level of beta cell mass obtained in step c) is reduced as compared to that of a healthy subject and diagnosing the subject as having hyperinsulinemia or being at risk of having hyperinsulinemia when the level of beta cell mass obtained in step c) is increased as compared to that of a healthy subject, or of a previous analysis of the same subject.
11. The method according to aspect 10, wherein said labelled molecule is selected from the group comprising: an antibody or a fragment thereof, a nanobody, an affibody, a diabody, a minibody, a single chain antibody, an aptamer, a photoaptamer, a peptide, a small molecule, an interacting partner, an isotopically labelled tracer, or a ligand, specifically binding to DPP6, especially to the extracellular domain of DPP6-K.
In preferred embodiments, said labelled molecule is radio-isotopically labelled.
In further preferred embodiments, said labelled molecule is fluorescently labelled.
Useful labels are known in the art and some non-limiting examples have been described herein elsewhere.
12. The method according to aspect 10 or 11, wherein said in vivo visualisation is done using a PET, PET-CT, SPECT or MRI scan, or through fluorescent imaging.
13. The method of any of the aspects 10 to 12, wherein the beta-cell-related disorder is type 1 diabetes mellitus, type 2 diabetes mellitus, hyperinsulinemia, obesity, or occurrence of insulinoma.
14. A labelled molecule, specifically binding to the extracellular domain of DPP6-K, for use in diagnosis of a beta-cell-related disorder in vivo, according to the method of any one of aspects 10 to 13, preferably wherein the beta-cell-related disorder is type 1 diabetes mellitus, type 2 diabetes mellitus, hyperinsulinemia, obesity, or occurrence of insulinoma.
15. A kit for (use in) visualising beta cells, for (use in) specifically measuring beta cell-mass, for (use in) diagnosing a beta-cell-related disorder, for (use in) detecting beta cell fragments in a blood or urine sample, and/or for (use in) purifying beta cells in a subject comprising a labelled molecule specifically binding to the extracellular domain of DPP6-K, preferably wherein said binding molecule is an antibody or a fragment thereof, a nanobody, an affybody, a single chain antibody, an aptamer, a photoaptamer, a peptide, a small molecule, an interacting partner, an isotopically labelled tracer, or a ligand, specifically binding to the extracellular domain of DPP6-K.
16. The method use or kit of any of the previous aspects, wherein the binding molecule is a nanobody comprising the binding pocket having CDR regions defined by SEQ ID No 9-11, more preferably wherein the binding molecule is a nanobody comprising the heavy chain variable domain as defined in SEQ ID NO. 8.
17. A method for following up the success of the transplantation of beta cells in a subject comprising the following steps:
    a) measuring the amount of beta-cell mass in the subject at one or more time points after transplantation of the subject with beta cells with the method according to aspect 5,
    b) determining the success of the transplantation by comparing the beta cell mass in the course of time by evaluating the evolution of beta-cell mass over time. In a preferred embodiment of said aspect, said measuring of the amount of beta-cell mass in the subject comprises the steps of:
       i) labelling beta cells in a sample based on presence of the DPP6-K variant, and
       ii) detecting or visualising the labelled beta cells. Said method can be carried out in vivo and/or in vitro.
18. A method for purifying or isolating beta cells from other pancreatic non-beta cells comprising the following steps:
    a) tagging the beta cells with a labelled binding molecule specifically binding to the extracellular domain of DPP6-K,
    b) isolating the labelled cells from the non-labelled cells through the tag on the beta cells, thereby obtaining a substantially pure beta cell preparation. Preferably said method is carried out in vitro.
19. A method for identification of regeneration of beta cells comprising the steps of:
    a) tagging the beta cells with a labelled binding molecule specifically binding to the extracellular domain of DPP6-K, b) isolating the labelled cells from the non-labelled cells through the tag on the beta cells, thereby obtaining a substantially pure regenerated beta cell preparation
c) performing immunohistochemistry to identify the number of newly regenerated beta cells, and to define the new beta cell mass
d) follow up of therapeutic strategies and detect beta cell mass recovery.

Preferably said method is carried out in vitro.

20. The method of aspect 18 or 19, wherein the tag is a magnetic bead, or paramagnetic bead. In a preferred embodiment, beta cell mass can be measured with MRI (Magnetic Resonance Imaging).

21. A method of identification of stem cell populations treated to differentiate towards functional insulin-expressing beta stem cells comprising the following steps:
a) tagging the treated stem cells with a labeled binding molecule specifically binding to the extracellular domain of DPP6-K,
b) isolating the labeled cells from the non-labeled cells through the tag on the potential beta stem cells, thereby obtaining a substantially pure beta stem cell preparation. Preferably said method is carried out in vitro.

22. The method of aspect 21, further comprising the steps of:
c) performing immunohistochemistry to identify the number of beta stem cells, and optionally to define the new beta cell mass; and/or
d) following-up op therapeutic strategies and detect newly formed beta cells.

23. A method for identifying new tracer molecules that specifically bind beta cells comprising the steps of:
a) contacting the candidate tracer molecule with cells or cell-lines positive for the extracellular domain of DPP6-K and measuring the interaction between the candidate tracer molecule and the cells;
b) contacting the candidate tracer molecule with cells or cell-lines negative for the extracellular domain of DPP6-K and measuring the interaction between the candidate tracer molecule and the cells;
c) comparing the interactions between both steps a) and b); and
d) retain these candidate tracer molecules that bind the cells of step a) but not the cells of step b) as beta-cell-mass tracer molecules. Preferably said method is carried out in vitro.

24. The method of aspect 23, wherein the DPP6 positive cell or cell-line is selected from the group comprising: rodent pancreatic islets, rat INS-1E cells, Kelly tumor cells and the human beta cell line ENDOC-BH1; and wherein the DPP6 negative cell-types or cell-lines are PANC-1 or CAPAN-2.

25. A kit for identifying new tracer molecules that specifically bind beta cells comprising two cell types or cell-lines, one being a cell-type or cell-line positive for the extracellular domain of DPP6-K and one being a cell-type or cell-line negative for the extracellular domain of DPP6-K.

26. The kit of aspect 25, wherein the cell-type or cell-line positive for the extracellular domain of DPP6-K is selected from the group comprising: rodent pancreatic islets, rat INS-1E cells, Kelly tumor cells, and the human beta cell line ENDOC-BH1; and/or wherein the cell-types or cell-lines negative for the extracellular domain of DPP6-K are PANC-1 or CAPAN-2.

27. A method for identifying new tracer molecules that specifically bind beta cells comprising the steps of:
a) contacting the candidate tracer molecule with a molecule representing the extracellular domain of DPP6-K and
b) measuring the interaction between the candidate tracer molecule and the DPP6 variant molecule, wherein these candidate tracer molecules that specifically bind the DPP6 variant molecule of step a) are retained as beta cell tracer molecules. Preferably said method is carried out in vitro.

28. A binding molecule specifically binding to the extracellular domain of DPP6-K, preferably selected from the group comprising: an antibody or a fragment thereof, a nanobody, an affibody, a diabody, a minibody, a single chain antibody, an aptamer, a photoaptamer, a peptide, a small molecule, an interacting partner, an isotopically labelled tracer, or a ligand specifically binding to the extracellular domain of DPP6-K. More particularly, said binding molecule is used for diagnosing T1D, monitoring T1D disease progression and/or monitoring T1D disease treatment, or in monitoring beta cell transplants in the skin intramuscular, or in other accessible locations of the subject.

29. The binding molecule according to aspect 28, which is a nanobody comprising CDR regions defined by SEQ ID Nos 9, 10, and 11.

30. The binding molecule according to aspect 28, which is a nanobody comprising the heavy chain variable domain defined by SEQ ID No 8.

31. A kit comprising binding molecules according to any one of aspects 28 to 30. More particularly, said kit is used for diagnosing T1D, monitoring T1D disease progression and/or monitoring T1D disease treatment, or in monitoring beta cell transplants in the skin intramuscular, or in other accessible locations of the subject.

32. The kit according to aspect 31, wherein said binding molecules are immobilised on a solid support, such as a chip or microchip.

In some embodiments, said binding molecules are labelled, preferably with a radioisotope, a fluorescent moiety, a chemiluminescent moiety, a bioluminescent moiety, a chemifluorescent moiety or a metal or magnetic moiety. In one embodiment such a kit is an immunochemical detection kit such as an ELISA kit. In another embodiment, said kit comprises radio(isotopically)labelled binding molecules.

33. The kit according to aspect 31 or 32, further comprising one or more (micro)fluidic or microvortex-creating channels wherein said binding molecules are immobilised, whereon beta cells and/or beta cell debris can be bound and subsequently detected.

The DPP6-K variant biomarker as defined herein is interesting because of its specificity for pancreatic beta cells. Even if some cross-reactivity would exist of the identified binding molecules with other variants of DPP6 sharing the same extracellular domain (cf. FIG. 2: e.g. DPP6-L, DPP6-006 and to some extent DPP6-007) such as those present on alpha cells, said binding molecules could be easily used to detect circulating and degrading beta cells and/or beta cell debris in a specific manner since alpha cells are not destroyed in type 1 diabetes and hence will not be detected in circulation. The use of binding molecules specific for DPP6 expressed on beta cells is important since it will enable the detection of beta cell debris and hence detect beta cell damage during e.g. T1D.

34. The invention hence further provides a method of diagnosing T1D using a kit comprising binding molecules specific for the extracellular domain of DPP6-K, as defined herein. In such a method, detection of beta cells and/or beta cell debris in the circulation of a subject is indicative of T1D disease development.

35. The invention further provides a method of monitoring T1D disease progression using a kit comprising binding molecules specific for the extracellular domain of DPP6-K as defined herein. In such a method, an increased detection over timed of beta cells and/or beta cell debris in the circulation of the subject is a measure for disease progression.

36. The invention further provides a method for monitoring T1D disease treatment using a kit comprising binding molecules specific for the extracellular domain of DPP6-K as defined herein. In such a method, a decrease in detection of beta cells and/or beta cell debris is a measure for disease improvement and hence of successful treatment.

37. The invention further provides a method of monitoring beta cell transplants in the skin, intramuscular, or in other accessible locations, using the binding molecule according to any one of aspects 28 to 30 or the kit according to any one of aspects 31 to 33, comprising the detection of the labelled binding molecule(s) specific for beta cells, preferably fluorescently labelled binding molecules, using non-invasive clinical imaging methods.

38. Use of the binding molecule according to claim 28, or of the kit according to any one of the preceding aspects, for delivering therapeutic agents specifically to beta cells, with the goal of protecting these cells against dysfunction and death in diabetes.

BRIEF DESCRIPTION OF THE DRAWINGS

FIG. 4A) Quantitative RT-PCR (qPCR) of HsDPP6 mRNA expression in EndoC-βH1 cells and human pancreatic islets exposed or not to cytokines (IL-1β and IFNγ) for 48 h as compared to HsDPP6 mRNA expression in 14 normal human tissues. The expression of HsDPP6 was higher in human pancreatic islets and EndoC-βH1 cells than in the other tissues. FIG. 4B) Densitometry analysis of western blots with EndoC-βH1 cells under control condition or following a 48 h exposure to cytokines (IL-1β and IFNγ). Here, Alpha-Tubulin was used as a reference protein, n=5. For the qPCR, unpaired one way ANOVA with Bidak correction for multiple comparisons was performed. EndoC-βH1 (with or without cytokines), n=5; human pancreatic islets (with or without cytokines), n=3; all other human tissues, n=1; *=p<0.05. Human islets and EndoC-βH1 cells preferentially express DPP6, as compared to other tissues, and this is not modified by pro-inflammatory cytokines.

FIG. 5A) Human pancreatic islets express mainly the DPP6-001 NM_001039350 (DPP6-K) variant, but they also express to a lesser extent DPP6-003, NM_130797, (DPP6-L), DPP6-006, NM_001936, (DPP6-S) and DPP6-007, NM_001290252. FIG. 5B) EndoC-βH1 cells express at the same level both DPP6-001 (DPP6-K) and DPP6-006 (DPP6-S), but they also express at a lower level DPP6-007. FIG. 5C) Expression of DPP6-001 in other human tissues; the highest extra-pancreatic expression is seen in brain, colon and thyroid. FIG. 5D) Expression of DPP6-003 in human tissues; the highest extra-pancreatic expression is observed in the thyroid. EndoC-βH1 with or without cytokines n=5; human pancreatic islets with or without cytokines n=10; other tissues, n=1. One way ANOVA with Bidak correction for multiple comparisons was performed. *=p<0.05, **=p<0.01.

FIGS. 6A-6C—SCID CB-17/Icr-Prkdcscid/Rj (SCID-EndoC)-Endoc-BH1 grafted mice. The EndoC-βH1 tumor bearing mice displayed hypoglycemia when the EndoC-βH1 tumors became palpable, the hypoglycemia was prevented with glucose-supplemented water. This was necessary as the EndoC-βH1 is a cell line that releases human insulin and human C-peptide at least in part in a non-regulated way. (FIG. 6A) EndoC-βH1 inoculated mice had a normal weight gain, in FIG. 6A SCID-EndoC mice, n=24; (FIG. 6B) Random glycemic values taken before inoculation, when the tumor became palpable after 9-10 weeks, and when the mice were fed with glucose supplemented water, SCID-EndoC mice, n=10-24; (FIG. 6C) Human C-peptide in serum from mice bearing an EndoC-βH1 tumor, SCID CB-17, n=22; SCID-EndoC mice, n=10. One way ANOVA with Bidak correction for multiple comparisons was performed to compare 3 groups, while unpaired Student's t-test was performed to compare two groups. *=p<0.05, =p<0.01, **=p<0.0001. These data confirms that the human insulin-producing cells engraft and are functional in SCID mouse.

FIG. 7—Sequences of exemplary nanobody 4hD29 identified as being highly specific for the extracellular domain of DPP6. The sequence is annotated with the IMGT numbering (international ImMunoGeneTics information system), indicating the CDRs accordingly. SEQ ID No 8 represents the sequence of the 4hD29 nanobody. The CDRs of said nanobody are also represented and correspond respectively to SEQ ID Nos. 9 to 11.

FIG. 15B: tumor uptake; tumor/blood ratio; and tumor/muscle ratio of 4hD29 and control (anti Bcl-10) nanobody.

DETAILED DESCRIPTION OF THE PREFERRED EMBODIMENTS

Figure 1:
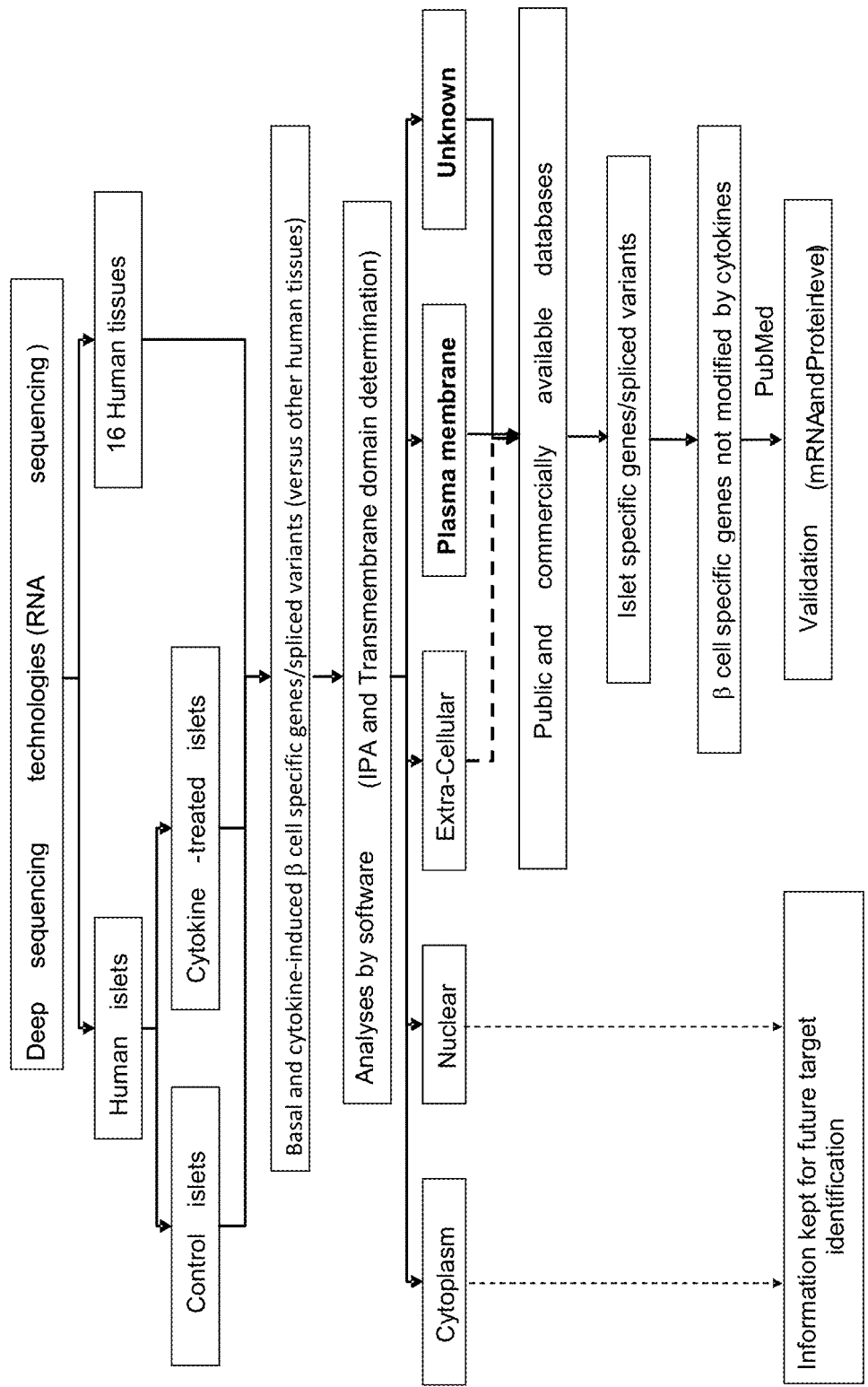
FIG. 1—Strategy for the screening of putative beta cell biomarkers. Detailed knowledge on the global alternative splicing of human islets was obtained via RNA sequencing, under both control condition and following exposure to pro-inflammatory cytokines (IL-1β+IFN-γ). Following this step, beta cell-specific and cytokine-independent alternative splicing isoforms (as compared to other 16 human tissues and cytokine-treated islets) were selected. Cell localization was then evaluated by using the IPA program in combination with other similar programs, and putative beta cell plasma membrane encoding alternative splicing variants were selected; spliced forms listed as "unknown" were also retained for additional analysis. The remaining mRNAs were then analyzed regarding their response to cytokines during deep sequencing analysis, and only mRNAs with little (less than 50%) change in expression following cytokine exposure were retained (the rationale here was to remove biomarkers that are potentially modified during insulitis). This was followed by literature search of the selected genes/proteins to further evaluate their suitability as targets for imaging, and then validation at the mRNA and protein level, based on real time RT-PCR, Western blot and immunohistochemistry in human pancreas and other relevant tissues (with particular attention to intra-abdominal organs, that may affect BCM imaging, and immune cells, that may infiltrate the islets during insulitis; expression of the target in extra-abdominal organs such as brain is not an exclusion criteria). Validated targets are then utilized for tracer development.

The present invention is directed to biomarkers specifically useful for visualizing pancreatic beta cells.

Said biomarkers are not only specific for pancreatic islets versus exocrine tissue but a number of extra selection criteria were added which makes these biomarker candidates more suitable for the use in beta cell imaging and targeting. Unique datasets were used containing quantitative information (instead of comparative information) to select the biomarker. The unique features assigned to the selected biomarkers are:

1. The selected biomarker candidate is enriched more than 50-100 times in human islets versus total human pancreas: Instead of using comparative data obtained by microarray, we have quantitative data obtained by RNA sequencing. Since islets constitute 1-2% of the total pancreas, we used as selection criteria an enrichment of 50-100 times in islets versus pancreas. Using the quantitative data we can calculate how many times the expression will be enriched in human pancreatic islets versus the surrounding human tissues (stomach, spleen, intestine) or versus tissues used for placing islet grafts (liver, kidney) based on comparison with publicly available human RNA-seq datasets; this is a very useful criteria for anticipating background levels and for selecting islet specific candidates. The enrichment in islets versus total pancreas is preferably higher than 50 fold.

2. Selected candidate is enriched in purified rat beta cells compared to purified rat non beta cells making them relatively beta cell specific. The islet composition changes during the evolution of T1D due to loss of beta cells and the relative increase in non beta cells (mostly alpha cells). It is thus crucial for quantification of beta cell mass that putative biomarkers are specifically expressed in beta cells. The present selection was done based on our unique data set obtained with RNA-seq. Until now no such selection has been done. The term "enriched" means that a higher level of expression is obtained in beta cells when compared to non-beta cells, manipulated under identical conditions. As this analysis is done based on RNA-seq, the FC change is not taken in account so we selected genes that were higher expressed in beta cells than in non-beta cells but no FC criteria was set as such.

3. The selected biomarker is well expressed in beta cells. For imaging the targets need to be expressed in sufficient amount on the pancreatic beta cells to enable detection. We have both quantitative data in human islets and comparative data in human islets and primary rat beta cells to check this criterion.

4. The selected biomarker is located in the plasma membrane and can be used for targeting with specific antibodies, chemical synthesis, natural compounds or with peptides. Antibodies and peptides targeting these proteins detect native structures located on the plasma membrane proteins with an affinity high enough to perform imaging/targeting. The localization in the plasma membrane was assessed by a Systems Biology approach (IPA analysis, GO analysis, literature screening) and we perform immunohistochemistry to confirm this localization.

5. The expression level of the selected gene/protein is not substantially modified (e.g. induced) during inflammation: We have a large amount of RNA-seq and microarray data comparing control condition to conditions in which inflammation is induced (e.g. cytokine-treated or virus- or dsRNA-exposed beta cells). During inflammation pancreatic beta cells often express similar markers as those found in immune cells (T-cells, dendritic cells) infiltrating in the pancreas. It is thus of major importance to select biomarkers exclusively expressed in the beta cells and not induced during inflammation in order to quantify beta cell mass. By comparison of our RNA-seq and microarray datasets with the publicly available Illumine database we could confirm these data. This analysis was not done previously by other groups. The term "not substantially modified (e.g. induced)" means that the expression level of the candidate marker is not induced in inflammatory versus non-inflammatory conditions. This is to counter the possible effect of inflammation increasing the expression in an equal amount of decrease in beta cell-mass due to a disease condition such as diabetes. (i.e. if the decrease in beta cell mass in diabetic conditions would be about 30% and the marker as such has an increased expression of about 30% due to inflammation condition, this would not allow to detect changes in beta cell mass based on said marker).

Next, a procedure was developed to analyze the best candidate of our list at the protein level and to confirm islet- and beta cell-specificity. For the selected candidate we prepared antibodies specifically targeting the biomarker. The selected candidate and the antibodies targeting the candidate were tested in human tissue microarrays confirming their specificity for pancreas (versus surrounding tissues) and their specific expression in pancreatic islets versus exocrine tissue. The protein expression of the biomarker was subsequently validated for its specificity to beta cells versus non beta cells via immunocytochemistry on pancreatic slices of normal and diseased human and rodent pancreas.

With this set of criteria a unique biomarker was obtained selectively expressed on the plasma membrane of human and rodent pancreatic beta cells. The expression level is high enough to perform imaging/targeting and the expression level is not substantially modified by inflammation and diabetic conditions or has not been previously identified as auto-antigen. This makes it a perfect candidate for imaging/targeting of beta cells.

The great advantage of the present invention is to enable determination of pancreatic beta cell mass in diabetes mellitus (see below). Of note, there are presently no other available methods to specifically measure beta cell mass.

Similarly, said biomarker can, due to its specificity be used as a marker for detecting damaged or degraded beta cells circulating in the body of the subject. Such a circulation marker is highly sought after in the field of diabetes mellitus diagnosis, progression monitoring and treatment.

Type 1 diabetes (T1D) is an autoimmune disease in which the body's immune system attacks and kills its own insulin-producing beta cells and kills them. A key obstacle to early detection of T1D, to understand the evolution of the disease and to assess the effectiveness of novel therapeutic interventions to prevent or cure the disease is the lack of direct, noninvasive technologies to visualize and measure beta cell mass.

Type 2 diabetes (T2D) is a long-term metabolic disorder that is characterized by high blood sugar caused by failure of the beta cells to compensate for insulin resistance, most commonly secondary to obesity. The lack of reliable methods to determine beta cell mass also limits follow up of pancreatic islet transplantation and of patients affected by type 2 diabetes (T2D), a disease where a progressive decrease of beta cell mass (albeit of less magnitude than T1D) is also present. To achieve the goal of beta cell imaging, there is an urgent need for beta cell specific membrane proteins which can be visualized. To solve this problem, we have selected a novel candidate beta cell biomarker by a Systems Biology approach. The results obtained indicate that:

The selected candidate is highly enriched in human pancreatic beta cells. Antibodies, Nanobodies® (Ablynx NV), small molecules or peptides directed against them can be made into tracers to be used for PET or MRI or SPECT imaging. These tracers will bind preferentially to beta cells, enabling very good specificity and selectivity. In later stages of T1D, when there is a severe decrease in the number of beta cells and a relative increase in alpha cells, beta cell specific biomarker will allow quantification of the remaining beta cell mass without background from non beta cells.

This biomarker will also allow follow up of pancreatic islet transplants, examination of the progressive decrease in beta cell mass in type 2 diabetic patients or of an eventual increase in beta cell mass in obese non-diabetic patients (in this case, there is an increase in beta cell mass that compensates for the insulin resistance).

The selected biomarker is not induced by inflammation and will not target infiltrating immune cells. Beta cells express autoantigens which are detected by infiltrating immune cells. Since we compare the expression of our selected biomarker in control and inflamed beta cells and select membrane proteins which are not expressed in immune cells we will be able to follow the beta cell mass during inflammation (insulitis)

The selected candidate allow non invasive imaging of islet grafts following human islet transplantation and allow adjustment of immunosuppressive therapy to support graft survival and earlier interventions with the aim of rescuing transplants, which are under augmented immune assault.

Endogenous antibodies targeting the candidates, arising as part of the autoimmune process in T1D, are valuable markers of autoimmunity and help in the detection of patients at a high risk to develop the disease.

The current agents used for imaging the pancreas include reagents such as glibenclamide, dopamine, fluorodeoxyglucose, fluorodithizone and DOPA. The uptake of these agents in beta cells, as compared to exocrine pancreas and non beta cells in the islets, is not sufficient to allow reliable imaging of beta-cell mass (Sweet et al, 2004).

In conclusion, the biomarker is preferentially expressed in beta cells and is expressed on the surface in sufficient amounts to enable imaging. It has extracellular domains against which a naturally occurring ligand, a peptide or and antibody (or antibody fragment) can be developed as tracer. The selected biomarker will not be modified in conditions of inflammation. These unique features will make clinical analysis of beta cell mass possible.

The goal of the biomarker of the present invention is its use in the estimation and visualisation of the pancreatic beta cell mass in healthy and diseased state (diabetes or following islet transplantation). The invention will allow the development of tools for prediction and follow up of the diabetic state, for the follow up of islet transplantation, and as surrogate markers for therapeutic assays aiming to prevent diabetes and/or regenerate beta cell mass. The non-invasive imaging performed with this candidate will allow the detection of the increase of decrease in beta cell mass.

The invention therefore provides a non-invasive method for the diagnosis, prognosis, progression monitoring, or treatment monitoring of a diabetic disorder such as type 1 or type 2 diabetes mellitus (T1D or T2D) or hyperinsulinemia, by detecting and/or measuring the beta cell mass of a subject and comparing it to a reference amount of beta cell mass of a healthy subject or of a subject with known diagnosis, prognosis, disease progression or treatment outcome. An increase of the beta cell mass in the subject under investigation points to a condition of hyperinsulinemia, while a reduction of the beta cell mass in the subject under investigation points to a condition of diabetes mellitus of type 1 or 2.

The non-invasive method for the diagnosis or prognosis of a diabetic disorder encompasses the highly specific detection and/or visualization of beta cells through the detection of beta cell-specific biomarker DPP6-K.

Figure 2:
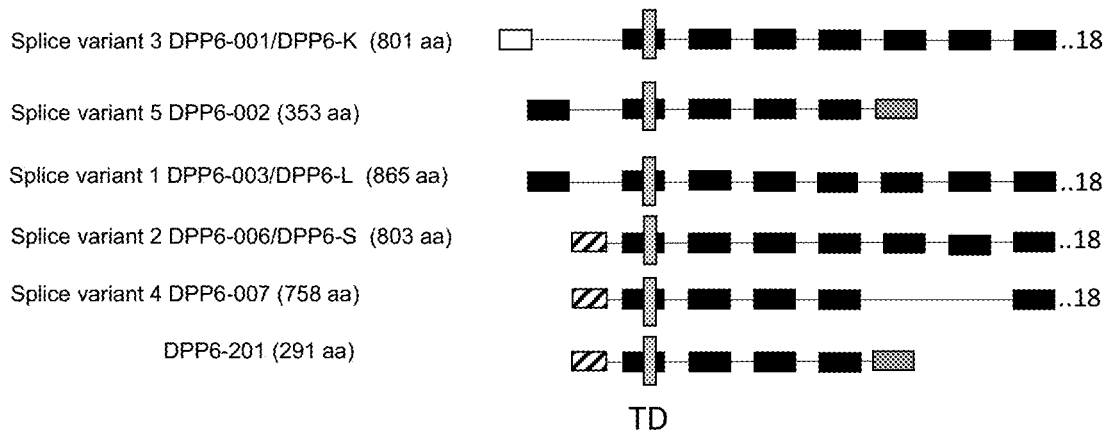
FIG. 2—DPP6 splice variants. TD denotes the transmembrane domain. Four of the variants are shortened and a numerical value is inserted instead of exons. Variant 3, NM_001039350, as used herein is depicted as DPP6-K, comprising 801 amino acids as defined in NP_001034439.1 (SEQ ID No. 1).

The term "DPP6" as used herein refers to the dipeptidyl peptidase VI protein encoded by the DPP6 gene. DPP6 is a single-pass type II transmembrane protein, which is highly expressed in the human and mouse brain. Not much is known about this protein except that it physically associates with certain ion channels in the brain and that DPP6 mutations are associated with brain pathologies. DPP6 is reported to be differentially-spliced, yielding 6 splice variants (FIG. 2). DPP6 expression is not modified by cytokines, a model of inflammation, which occurs during T1D pathogenesis, which has been confirmed on the RNA level as well as on the protein level by western blot of EndoC-B1H cells treated with cytokines (not shown). The DPP6-K variant (also called DPP6-001, or isoform 3 of DPP6) is defined by genbank entry NM_001039350, comprising 801 amino acids. Since most DPP6 variants only differ in their intracellular region, the extracellular regions which are generally targeted by antibodies and antibody-derivatives are the same. DPP6-K is characterized by the 801 amino acid sequence depicted by SEQ ID No.1 derived from NCBI Ref Seq NP_001034439.1 (dipeptidyl aminopeptidase-like protein 6 isoform 3 [*Homo sapiens*]). The corresponding mouse DPP6 protein variant is characterized by SEQ ID No.2, derived from NCBI Ref Seq AAH85154.1 (Dpp 6 protein [Mus musculus]). For obtaining specific binding molecules (e.g. antibodies or nanobodies), the DPP6 extracellular domain peptide characterized by SEQ ID No. 3 was used (underlined in the sequence of SEQ ID NO1 below). This will yield binding molecules recognizing the extracellular domain of DPP6, particularly of DPP6-K, DPP-L, and DPP6-006.

```
                                                         (SEQ ID NO. 1)
MKEKAMIKTA KMQGNVMELV GSNPPQRNWK GIAIALLVIL VICSLIVTSV ILLTPAEDNS

LSQKKKVTVE DLFSEDFKIH DPEAKWISDT EFIYREQKGT VRLWNVETNT STVLIEGKKI

ESLRAIRYEI SPDREYALFS YNVEPIYQHS YTGYYVLSKI PHGDPQSLDP PEVSNAKLQY

AGWGPKGQQL IFIFENNIYY CAHVGKQAIR VVSTGKEGVI YNGLSDWLYE EEILKTHIAH

WWSPDGTRLA YAAINDSRVP IMELPTYTGS IYPTVKPYHY PKAGSENPSI SLHVIGLNGP

THDLEMMPPD DPRMREYYIT MVKWATSTKV AVTWLNRAQN VSILTLCDAT TGVCTKKHED

ESEAWLHRQN EEPVFSKDGR KPFFIRAIPQ GGRGKFYHIT VSSSQPNSSN DNIQSITSGD

WDVTKILAYD EKGNKIYFLS TEDLPRRRQL YSANTVGNFN RQCLSCDLVE NCTYFSASFS

HSMDFFLLKC EGPGVPMVTV HNTTDKKKMF DLETNEHVKK AINDRQMPKV EYRDIEIDDY

NLPMQILKPA TFTDTTHYPL LLVVDGTPGS QSVAEKFEVS WETVMVSSHG AVVVKCDGRG

SGFQGTKLLH EVRRRLGLLE EKDQMEAVRT MLKEQYIDRT RVAVFGKDYG GYLSTYILPA

KGENQGQTFT CGSALSPITD FKLYASAFSE RYLGLHGLDN RAYEMTKVAH RVSALEEQQF

LIIHPTADEK IHFQHTAELI TQLIRGKANY SLQIYPDESH YFTSSSLKQH LYRSIINFFV

ECFRIQDKLL TVTAKEDEEE D  (SEQ ID NO. 3 UNDERLINED)

(SEQ ID NO. 2)
MKEKAMIKTA KMQGNVMELV GSNPPQRNWK GIAIALLVIL VICSLIVTSV ILLTPAEDTS

LSQKKKVTVE DLFSEDFKIH DPEAKWISNK EFIYRERKGS VILRNVETNN STVLIEGKKI

ESLRAIRYEI SPDKEYVLFS YNVEPVYQHS HTGYYVLSKI PHGDPQSLDP PEVSNAKLQY

AGWGPKGQQL IFIFENNIYY CAHVGKQAIR VVSTGKEGVI YNGLSDWLYE EEILKSHIAH

WWSPDGTRLA YATINDSRVP LMELPTYTGS VYPTVKPYHY PKAGSENPSI SLHVIGLNGP

THDLEMMPPD DPRMREYYIT MVKWATSTKV AVTWLNRAQN VSILTLCDAT TGVCTKKHED

ESEAWLHRQN EEPVFSKDGR KFFFVRAIPQ GGRGKFYHIT VSSSQPNSSN DNIQSITSGD

WDVTKILSYD EKRNKIYFLS TEDLPRRRHL YSANTVDDFN RQCLSCDLVE NCTYVSASFS

HNMDFFLLKC EGPGVPTVTV HNTTDKRRMF DLEANEEVQK AINDRQMPKI EYRKIEVEDY

SLPMQILKPA TFTDTAHYPL LLVVDGTPGS QSVTERFEVT WETVLVSSHG AVVVKCDGRG
```

-continued

```
SGFQGTKLLQ EVRRRLGFLE EKDQMEAVRT MLKEQYIDKT RVAVFGKDYG GYLSTYILPA

KGENQGQTFT CGSALSPITD FKLYASAFSE RYLGLHGLDN RAYEMTKLAH RVSALEDQQF

LIIHATADEK IHFQHTAELI TQLIKGKANY SLQIYPDESH YFHSVALKQH LSRSIIGFFV

ECFRVQDKLP TATAKEEEEE D
```

The detection of the specific markers is done by using a radioisotopically labelled tracer molecule that binds the biomarker with high specificity. Tracers may for example be antibodies, or their fragments, single chain antibodies, nanobodies, affibodies, minibodies, diabodies, aptamers, photoaptamers, a specific ligand or interacting protein, or any small molecule or the like that has been shown to specifically bind the biomarker of choice.

The antibodies can be known or commercially available antibodies, or can be specifically designed to detect the biomarker of the invention in a highly specific manner.

In this respect, the inventors designed binding molecules directed to the extracellular domain of DPP6-K, e.g. by immunizing animals with the following peptide (SEQ ID NO: 3):

```
LTPAEDNSLS QKKKVTVEDL FSEDFKIHDP

EAKWISDTEF IYREQKGTVR

LWNVETNTST VLIEGKKIES LRAIRYEISP

DREYALFSYN VEPIYQHSYT

GYYVLSKIPH GDPQSLDPPE VSNAKLQYAG

WGPKGQQLIF IFENNIYYCA

HVGKQAIRVV STGKEGVIYN GLSDWLYEEE

ILKTHIAHWW SPDGTRLAYA

AINDSRVPIM ELPTYTGSIY PTVKPYHYPK

AGSENPSISL HVIGLNGPTH

DLEMMPPDDP RMREYYITMV KWATSTKVAV

TWLNRAQNVS ILTLCDATTG

VCTKKHEDES EAWLHRQNEE PVFSKDGRKF

FFIRAIPQGG RGKFYHITVS

SSQPNSSNDN IQSITSGDWD VTKILAYDEK

GNKIYFLSTE DLPRRRQLYS

ANTVGNFNRQ CLSCDLVENC TYFSASFSHS

MDFFLLKCEG PGVPMVTVHN

TTDKKKMFDL ETNEHVKKAI NDRQMPKVEY

RDIEIDDYNL PMQILKPATF

TDTTHYPLLL VVDGTPGSQS VAEKFEVSWE

TVMVSSHGAV VVKCDGRGSG

FQGTKLLHEV RRRLGLLEEK DQMEAVRTML

KEQYIDRTRV AVFGKDYGGY

LSTYILPAKG ENQGQTFTCG SALSPITDFK

LYASAFSERY LGLHGLDNRA
```

```
YEMTKVAHRV SALEEQQFLI IHPTADEKIH

FQHTAELITQ LIRGKANYSL

QIYPDESHYF TSSSLKQHLY RSIINFFVEC

FRIQDKLLTV TAKEDEEED
```

In one embodiment, the diagnostic or prognostic method of the invention uses Positron Emission Tomography (PET), a nuclear medicine medical imaging technique which produces a three-dimensional image or map of functional processes in the body. The system detects pairs of gamma rays emitted indirectly by a positron-emitting radioisotope, which is introduced into the body through a tracer molecule e.g. a specific biomarker binding molecule. Images of the radioisotope labeled tracer in the body are then reconstructed by computer analysis. In modern scanners, a PET scan is combined with a CT X-ray scan (PET-CT) performed on the patient at the same time, in the same machine, providing the structural reference of the organs etc.

In an alternative embodiment, single photon emission computed tomography (SPECT) imaging can be used in the diagnostic or prognostic method of the invention. SPECT uses a gamma camera to acquire multiple 2-D projections from multiple angles. A computer is then used to apply a tomographic reconstruction algorithm to the multiple projections, yielding a 3-D dataset. This dataset may then be manipulated to show thin slices along any chosen axis of the body.

Preferred labels used in PET or PET-CT are short-lived radioisotopes such as carbon-11 (~20 min), nitrogen-13 (~10 min), oxygen-15 (~2 min), galium-68 (~68 minutes) and fluorine-18 (~110 min) or medium-lived radioisotopes such as zirconium-89 (~4 days) and iodine-124 (~4 days) when appropriate. Several novel tracer molecules have been developed including modified Exendin derivatives (Poly-Chelator Exendin, cleavable linkers and click-chemistry for easy 18F labelling), a PAC1 receptor targeting peptide, GIP derivatives for targeting the GIP receptor, a peptide targeting GPR54, and nanoparticles for MRI and optical imaging coupled with Exendin-4 and glibenclamide. GMP kits for clinical imaging for $^{111}$In and $^{68}$Ga labelling of Exendin have been developed, fully GMP certified, and can be distributed in Europe after approval of a certified person.

These novel tracers have been evaluated in vitro and in vivo. Poly-chelator-Exendin has identical pharmacokinetic properties when compared to the lead compound of the project but can be labelled with much higher specific activities, enabling improved small animal imaging with higher activity doses and injection of lower amounts of peptide (also for human use). Other tracers (GIP, PAC1 targeting peptide, GPR54 targeting peptide) do not appear to be suitable for in vivo imaging of pancreatic beta cells although in tumour imaging, PAC1 targeting peptide shows favourable results. Non-invasive islet imaging is also being developed with high field MRI and the use of nanoparticles and probes targeting beta cells via the lead compound as well as manganese contrast enhancement. xf-FDOCT has been further established as a new and powerful method to follow islets and diabetes progression in autoimmune diabetic mouse (NOD) models, to visualize blood flow in pancreatic islets and to dynamically monitor tracer distribution within the pancreas of live mice.

Preparation and assessment of the GMP clinical grade SPECT and PET tracer targeting GLP-1R is completed. Protocols for quantitative SPECT imaging have been implemented and optimized, as well as dosimetry protocols. Full documentation according to EMA standards for the Exendin based tracers has been achieved for clinical studies and the respective documents allow easy modification for use with other Exendin-based tracers (except for the production IMPD that needs to be prepared for every tracer molecule based on the labelling protocol). As already mentioned, the kits together with full documentation can now be distributed throughout Europe for multicenter studies after approval by a qualified person. Clinical trials with Exendin are under way.

A typical in vivo diagnostic method encompassed by the invention is as follows:

a) introducing an isotopically labelled tracer molecule, specifically binding to the beta cell specific biomarker into a subject, b) the in vivo visualisation of a tracer molecule specifically binding to the beta cells in the pancreas using PET, PET-CT or SPECT, c) quantification of the beta cells mass in said subject, d) comparison of the beta cell mass data obtained in step c) with the beta cell mass of a healthy subject, and e) diagnosing the subject as having diabetes or being at risk of having diabetes when the level of beta cell mass obtained in step c) is reduced as compared to that of a healthy subject and diagnosing the subject as having hyperinsulinemia or being at risk of having hyperinsulinemia when the level of beta cell mass obtained in step c) is increased as compared to that of a healthy subject.

The method of in vivo diagnosis or prognosis can be used to diagnose insulin-related disorders such as type 1 or type 2 diabetes mellitus, hyperinsulinemia and pancreatic cancer such as the occurrence of neuroendocrine tumors of the pancreas like insulinoma derived from the beta cells.

For treating insulin-related disorders, pancreatic islet transplantation is an option.

Typically, the Edmonton protocol is applied wherein specialized enzymes are used to remove islets from the pancreas of a deceased donor. Because the islets are fragile, transplantation occurs soon after they are removed. Typically a patient receives at least 10,000 islet "equivalents" per kilogram of body weight, extracted from two or more donor pancreases. Patients often require two transplants to achieve insulin independence. Some transplants have used fewer islet equivalents taken from a single donated pancreas. Transplants are often performed by a radiologist, who uses x rays and ultrasound to guide placement of a catheter through the upper abdomen and into the portal vein of the liver. The islets are then infused slowly through the catheter into the liver. The patient receives a local anesthetic and a sedative. In some cases, a surgeon may perform the transplant through a small incision, using general anesthesia.

The key of success for such a beta cell transplantation treatment is of course the purity of the beta cell preparation used for the transplantation. The invention provides for methods of specifically isolating beta cells for use in islet transplantation and tools for follow up of transplanted beta cells.

In a further embodiment, the invention provides for methods to isolate and/or purify pancreatic beta cells from pancreatic tissue, by visualizing or labeling the beta cells in a specific manner using the DPP6-K variant.

Alternatively, the method provides a method for identification of stem cell populations in order to derive functional insulin-expressing cells comprising the following steps:

a) tagging the treated stem cells with a labelled binding molecule specifically binding to the DPP6-K variant, b) isolating the labelled cells from the non-labeled cells through the tag on the potential beta stem cells, thereby obtaining a substantially pure beta stem cell preparation.

The method of the invention can in certain embodiments further comprise the steps of:

c) performing immunohistochemistry to identify the number of beta stem cells, and to define the new beta cell mass and d) follow up of therapeutic strategies and detect newly formed beta cell mass.

The above separation methods can for example be performed by separating labelled cells from non-labelled cells using standard separation techniques based on the retention of labelled binding molecules specifically binding to the biomarker of the present invention.

One option is to use antibodies, nanobodies, aptamers, oligonucleotides or other specific binding agents or ligands, specifically binding to the biomarker of the invention, for tagging cells of interest with a small magnetic particle or magnetic bead. The bead-binding molecule conjugate is then directed to the beta-cells in the pancreatic cell preparation and the beta cells can be specifically purified from the total pancreatic cell preparation by using e.g. an electromagnetic field. In some systems, the sample is processed through a column that generates a magnetic field when placed within the separator instrument, retaining only the labelled cells.

Other systems offer simplified versions of the magnetic separator. Instead of a column and separator instrument, these systems use a simple magnet to directly retain the labeled cells within the tube, while the supernatant is drawn off. Some of these systems can be used in a positive or negative selection manner. Negative or enrichment selection means that unwanted cells can be labeled (captured), leaving the cells of interest label-free. The magnetic particles do not interfere with flow cytometry, nor do they interfere with cell growth, according to Hammonds, so cells that have been isolated using such a system can be further cultured.

Magnetic separation has proven uniquely powerful and broadly applicable, sometimes leading to 70% recovery of the target cells and up to 98% purity while retaining cell viability.

Alternatively, an efficient non-magnetic separation method, based on work on tetrameric antibody complexes (TACs) works by linking unwanted cells in a sample together, forming clumps. After labelling, the sample is layered over a buoyant density medium such as Ficoll. The labelled cells pellet with when centrifuged, while the desired, unlabelled cells are recovered at the interface. This method is fast and the cells obtained are not labelled with antibodies and are untouched.

Many of these techniques are most powerful in combination. The skilled person would however be aware of other methods to selectively purify specific cell-types.

The term "binding molecules" used in the methods and kits of the invention refers to all suitable binding molecules that are specifically binding or interacting with the biomarker of the invention and that can be used in the methods and kits of the present invention. Examples of suitable binding agents are antibodies, monoclonal- or polyclonal antibodies, nanobodies, affybodies, antibody fragments, aptamers, photoaptamers, oligonucleotides, lipocalins, specifically interacting small molecules, Molecular Imprinting Polymers (MIPs), DARPins, ankyrins, specifically interacting proteins, peptidomimetics, biomimetics or peptides, and other molecules that specifically bind to the biomarker.

As used herein, the term 'antibody' refers to polyclonal antibodies, monoclonal antibodies, humanized antibodies, single-chain antibodies, and fragments thereof such as Fab, F(ab)2, Fv, and other fragments that retain the antigen binding function of the parent antibody. As such, an antibody may refer to an immunoglobulin or glycoprotein, or fragment or portion thereof, or to a construct comprising an antigen-binding portion comprised within a modified immunoglobulin-like framework, or to an antigen-binding portion comprised within a construct comprising a non-immunoglobulin-like framework or scaffold.

As used herein, the term 'monoclonal antibody' refers to an antibody composition having a homogeneous antibody population. The term is not limited regarding the species or source of the antibody, nor is it intended to be limited by the manner in which it is made. The term encompasses whole immunoglobulins as well as fragments and others that retain the antigen binding function of the antibody. Monoclonal antibodies of any mammalian species can be used in this invention. In practice, however, the antibodies will typically be of rat or murine origin because of the availability of rat or murine cell lines for use in making the required hybrid cell lines or hybridomas to produce monoclonal antibodies.

As used herein, the term 'polyclonal antibody' refers to an antibody composition having a heterogeneous antibody population. Polyclonal antibodies are often derived from the pooled serum from immunized animals or from selected humans.

'Heavy chain variable domain of an antibody or a functional fragment thereof', as used herein, means (i) the variable domain of the heavy chain of a heavy chain antibody, which is naturally devoid of light chains (also indicated hereafter as $V_{HH}$), including but not limited to the variable domain of the heavy chain of heavy chain antibodies of camelids or sharks or (ii) the variable domain of the heavy chain of a conventional four-chain antibody (also indicated hereafter as $V_H$), including but not limited to a camelized (as further defined herein) variable domain of the heavy chain of a conventional four-chain antibody (also indicated hereafter as camelized $V_H$) or any functional fragments thereof, such as but not limited to one or more stretches of amino acid residues (i.e. small peptides) that are particularly suited for binding to a tumor antigen and which are present in, and/or may be incorporated into, the $V_{HH}$'s as disclosed herein (or may be based on and/or derived from CDR sequences of the $V_{HH}$'s as disclosed herein).

As further described hereinbelow, the amino acid sequence and structure of a heavy chain variable domain of an antibody can be considered, without however being limited thereto, to be comprised of four framework regions or 'FR's', which are referred to in the art and hereinbelow as 'framework region 1' or 'FR1'; as 'framework region 2' or 'FR2'; as 'framework region 3' or 'FR3'; and as 'framework region 4' or 'FR4', respectively, which framework regions are interrupted by three complementary determining regions or 'CDR's', which are referred to in the art as 'complementarity determining region 1' or 'CDR1'; as 'complementarity determining region 2' or 'CDR2'; and as 'complementarity determining region 3' or 'CDR3', respectively.

An amino acid sequence, in particular an antibody fragment, such as a $V_{HH}$ or functional fragments thereof, as disclosed herein is considered to be '(in) essentially isolated (form)' as used herein, when it has been extracted or purified from the host cell and/or medium in which it is produced.

In respect of the amino acid sequences, in particular an antibody fragment, such as a $V_H$ or functional fragments thereof $_H$, as disclosed herein, the terms 'binding region', 'binding site' or 'interaction site' present on the amino acid sequences as disclosed herein shall herein have the meaning of a particular site, region, locus, part, or domain present on the target molecule, which particular site, region, locus, part, or domain is responsible for binding to that target molecule. Such binding region thus essentially consists of that particular site, region, locus, part, or domain of the target molecule, which is in contact with the amino acid sequence when bound to that target molecule.

As used herein, the terms 'complementarity determining region' or 'CDR' within the context of antibodies refer to variable regions of either the H (heavy) or the L (light) chains (also abbreviated as VH and VL, respectively) and contain the amino acid sequences capable of specifically binding to antigenic targets. These CDR regions account for the basic specificity of the antibody for a particular antigenic determinant structure. Such regions are also referred to as "hypervariable regions." The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all canonical antibodies each have 3 CDR regions, each non-contiguous with the others (termed L1, L2, L3, H1, H2, H3) for the respective light (L) and heavy (H) chains.

As also further described hereinbelow, the total number of amino acid residues in a heavy chain variable domain of an antibody (including a $V_{HH}$ or a $V_H$) can be in the region of 110-130, is preferably 112-115, and is most preferably 113. It should however be noted that parts, fragments or analogs of a heavy chain variable domain of an antibody are not particularly limited as to their length and/or size, as long as such parts, fragments or analogs retain (at least part of) the functional activity, and/or retain (at least part of) the binding specificity of the original a heavy chain variable domain of an antibody from which these parts, fragments or analogs are derived from. Parts, fragments or analogs retaining (at least part of) the functional activity, and/or retaining (at least part of) the binding specificity of the original heavy chain variable domain of an antibody from which these parts, fragments or analogs are derived from are also further referred to herein as 'functional fragments' of a heavy chain variable domain.

The amino acid residues of a variable domain of a heavy chain variable domain of an antibody (including a $V_{HH}$ or a $V_H$) are numbered according to the IMGT numbering (international ImMunoGeneTics information system). Hence, in the present description, aspects, claims and figures, the numbering according to IMGT as applied to $V_{HH}$ domains will be followed, unless indicated otherwise.

For a general description of heavy chain antibodies and the variable domains thereof, reference is inter alia made to the following references, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx NV; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551 by Ablynx NV and the further published patent applications by Ablynx NV; Hamers-Casterman et al., Nature 1993 Jun. 3; 363 (6428): 446-8; Davies and Riechmann, FEBS Lett. 1994 Feb. 21; 339(3): 285-90; Muyldermans et al., Protein Eng. 1994 September; 7(9): 1129-3; Davies and Riechmann, Biotechnology (NY) 1995 May; 13(5): 475-9; Gharoudi et al., 9th Forum of Applied Biotechnology, Med. Fac. Landbouw Univ. Gent. 1995; 60/4a part I: 2097-2100; Davies and Riechmann, Protein Eng. 1996 June; 9(6): 531-7; Desmyter et al., Nat Struct Biol. 1996 September; 3(9): 803-11; Sheriff et al., Nat Struct Biol. 1996 September; 3(9): 733-6; Spinelli et al., Nat Struct Biol. 1996 September; 3(9): 752-7; Arbabi Ghahroudi et al., FEBS Lett. 1997 Sep. 15; 414(3): 521-6; Vu et al., Mol. Immunol. 1997 November-December; 34(16-17): 1121-31; Atarhouch et al., Journal of Carvel Practice and Research 1997; 4: 177-182; Nguyen et al., J. Mol. Biol. 1998 Jan. 23; 275(3): 413-8; Lauwereys et al., EMBO J. 1998 Jul. 1; 17(13): 3512-20; Frenken et al., Res Immunol. 1998 July-August; 149(6):589-99; Transue et al., Proteins 1998 Sep. 1; 32(4): 515-22; Muyldermans and Lauwereys, J. Mol. Recognit. 1999 March-April; 12 (2): 131-40; van der Linden et al., Biochim. Biophys. Acta 1999 Apr. 12; 1431(1): 37-46; Decanniere et al., Structure Fold. Des. 1999 Apr. 15; 7(4): 361-70; Ngyuen et al., Mol. Immunol. 1999 June; 36(8): 515-24; Woolven et al., Immunogenetics 1999 October; 50 (1-2): 98-101; Riechmann and Muyldermans, J. Immunol. Methods 1999 Dec. 10; 231 (1-2): 25-38; Spinelli et al., Biochemistry 2000 Feb. 15; 39(6): 1217-22; Frenken et al., J. Biotechnol. 2000 Feb. 28; 78(1): 11-21; Nguyen et al., EMBO J. 2000 Mar. 1; 19(5): 921-30; van der Linden et al., J. Immunol. Methods 2000 Jun. 23; 240 (1-2): 185-95; Decanniere et al., J. Mol. Biol. 2000 Jun. 30; 300 (1): 83-91; van der Linden et al., J. Biotechnol. 2000 Jul. 14; 80(3): 261-70; Harmsen et al., Mol. Immunol. 2000 August; 37(10): 579-90; Perez et al., Biochemistry 2001 Jan. 9; 40(1): 74-83; Conrath et al., J. Biol. Chem. 2001 Mar. 9; 276 (10): 7346-50; Muyldermans et al., Trends Biochem Sci. 2001 April; 26(4):230-5; Muyldermans S., J. Biotechnol. 2001 June; 74 (4): 277-302; Desmyter et al., J. Biol. Chem. 2001 Jul. 13; 276 (28): 26285-90; Spinelli et al., J. Mol. Biol. 2001 Aug. 3; 311 (1): 123-9; Conrath et al., Antimicrob Agents Chemother. 2001 October; 45 (10): 2807-12; Decanniere et al., J. Mol. Biol. 2001 Oct. 26; 313(3): 473-8; Nguyen et al., Adv Immunol. 2001; 79: 261-96; Muruganandam et al., FASEB J. 2002 February; 16 (2): 240-2; Ewert et al., Biochemistry 2002 Mar. 19; 41 (11): 3628-36; Dumoulin et al., Protein Sci. 2002 March; 11 (3): 500-15; Cortez-Retamozo et al., Int. J. Cancer. 2002 Mar. 20; 98 (3): 456-62; Su et al., Mol. Biol. Evol. 2002 March; 19 (3): 205-15; van der Vaart J M., Methods Mol. Biol. 2002; 178: 359-66; Vranken et al., Biochemistry 2002 Jul. 9; 41 (27): 8570-9; Nguyen et al., Immunogenetics 2002 April; 54 (1): 39-47; Renisio et al., Proteins 2002 Jun. 1; 47 (4): 546-55; Desmyter et al., J. Biol. Chem. 2002 Jun. 28; 277 (26): 23645-50; Ledeboer et al., J. Dairy Sci. 2002 June; 85 (6): 1376-82; De Genst et al., J. Biol. Chem. 2002 Aug. 16; 277 (33): 29897-907; Ferrat et al., Biochem. J. 2002 Sep. 1; 366 (Pt 2): 415-22; Thomassen et al., Enzyme and Microbial Technol. 2002; 30: 273-8; Harmsen et al., Appl. Microbiol. Biotechnol. 2002 December; 60 (4): 449-54; Jobling et al., Nat. Biotechnol. 2003 January; 21 (1): 77-80; Conrath et al., Dev. Comp. Immunol. 2003 February; 27 (2): 87-103; Pleschberger et al., Bioconjug. Chem. 2003 March-April; 14 (2): 440-8; Lah et al., J. Biol. Chem. 2003 Apr. 18; 278 (16): 14101-11; Nguyen et al., Immunology. 2003 May; 109 (1): 93-101; Joosten et al., Microb. Cell Fact. 2003 Jan. 30; 2 (1): 1; Li et al., Proteins 2003 Jul. 1; 52 (1): 47-50; Loris et al., Biol. Chem. 2003 Jul. 25; 278 (30): 28252-7; van Koningsbruggen et al., J. Immunol. Methods. 2003 August; 279 (1-2): 149-61; Dumoulin et al., Nature. 2003 Aug. 14; 424 (6950): 783-8; Bond et al., J. Mol. Biol. 2003 Sep. 19; 332 (3): 643-55; Yau et al., J. Immunol. Methods. 2003 Oct. 1; 281 (1-2): 161-75; Dekker et al., J. Virol. 2003 November; 77 (22): 12132-9; Meddeb-Mouelhi et al., Toxicon. 2003 December; 42 (7): 785-91; Verheesen et al., Biochim. Biophys. Acta 2003 Dec. 5; 1624 (1-3): 21-8; Zhang et al., J Mol Biol. 2004 Jan. 2; 335 (1): 49-56; Stijlemans et al., J Biol. Chem. 2004 Jan. 9; 279 (2): 1256-61; Cortez-Retamozo et al., Cancer Res. 2004 Apr. 15; 64 (8): 2853-7; Spinelli et al., FEBS Lett. 2004 Apr. 23; 564 (1-2): 35-40; Pleschberger et al., Bioconjug. Chem. 2004 May-June; 15 (3): 664-71; Nicaise et al., Protein Sci. 2004 July; 13 (7): 1882-91; Omidfar et al., Tumour Biol. 2004 July-August; 25 (4): 179-87; Omidfar et al., Tumour Biol. 2004 September-December; 25(5-6): 296-305; Szynol et al., Antimicrob Agents Chemother. 2004 September; 48(9):3390-5; Saerens et al., J. Biol. Chem. 2004 Dec. 10; 279 (50): 51965-72; De Genst et al., J. Biol. Chem. 2004 Dec. 17; 279 (51): 53593-601; Dolk et al., Appl. Environ. Microbiol. 2005 January; 71(1): 442-50; Joosten et al., Appl Microbiol Biotechnol. 2005 January; 66(4): 384-92; Dumoulin et al., J. Mol. Biol. 2005 Feb. 25; 346 (3): 773-88; Yau et al., J Immunol Methods. 2005 February; 297 (1-2): 213-24; De Genst et al., J. Biol. Chem. 2005 Apr. 8; 280 (14): 14114-21; Huang et al., Eur. J. Hum. Genet. 2005 Apr. 13; Dolk et al., Proteins. 2005 May 15; 59 (3): 555-64; Bond et al., J. Mol. Biol. 2005 May 6; 348(3):699-709; Zarebski et al., J. Mol. Biol. 2005 Apr. 21.

Generally, it should be noted that the term 'heavy chain variable domain' as used herein in its broadest sense is not limited to a specific biological source or to a specific method of preparation. For example, as will be discussed in more detail below, the heavy chain variable domains derived from heavy chain antibodies (i.e. $V_{HH}$'s) as disclosed herein can be obtained (1) by isolating the $V_{HH}$ domain of a naturally occurring heavy chain antibody; (2) by expression of a nucleotide sequence encoding a naturally occurring $V_{HH}$ domain; (3) by 'camelization' (as described below) of a naturally occurring $V_H$ domain from any animal species, in particular a species of mammal, such as from a human being, or by expression of a nucleic acid encoding such a camelized $V_H$ domain; (4) by 'camelisation' of a 'domain antibody' or 'Dab' as described by Ward et al (supra), or by expression of a nucleic acid encoding such a camelized $V_H$ domain (5) using synthetic or semi-synthetic techniques for preparing proteins, polypeptides or other amino acid sequences; (6) by preparing a nucleic acid encoding a $V_{HH}$ using techniques for nucleic acid synthesis, followed by expression of the nucleic acid thus obtained; and/or (7) by any combination of the foregoing. Suitable methods and techniques for performing the foregoing will be clear to the skilled person based on the disclosure herein and for example include the methods and techniques described in more detail hereinbelow.

The term 'affinity', as used herein, refers to the degree to which a polypeptide, in particular an immunoglobulin, such as an antibody, or an immunoglobulin fragment, such as a $V_{HH}$, binds to an antigen so as to shift the equilibrium of antigen and polypeptide toward the presence of a complex formed by their binding. Thus, for example, where an antigen and antibody (fragment) are combined in relatively equal concentration, an antibody (fragment) of high affinity will bind to the available antigen so as to shift the equilibrium toward high concentration of the resulting complex. The dissociation constant is commonly used to describe the affinity between the protein binding domain and the antigenic target. Typically, the dissociation constant is lower than $10^{-5}$ M. Preferably, the dissociation constant is lower than $10^{-6}$ M, more preferably, lower than $10^{-7}$ M. Most preferably, the dissociation constant is lower than $10^{-8}$ M, such as lower than $10^{-9}$ M.

The terms 'specifically bind' and 'specific binding', as used herein, generally refers to the ability of a polypeptide, in particular an immunoglobulin, such as an antibody, or an immunoglobulin fragment, such as a $V_{HH}$ or functional fragments thereof, to preferentially bind to a particular antigen that is present in a homogeneous mixture of different antigens. In certain embodiments, a specific binding interaction will discriminate between desirable and undesirable antigens in a sample, in some embodiments more than about 10 to 100-fold or more (e.g., more than about 1000- or 10,000-fold).

Accordingly, an amino acid sequence, in particular an antibody fragment, such as a $V_{HH}$ or functional fragments thereof, as disclosed herein is said to 'specifically bind to' a particular target when that amino acid sequence has affinity for, specificity for and/or is specifically binding to that target (or for at least one part or fragment thereof).

An amino acid sequence, in particular an antibody fragment, such as a $V_{HH}$ or functional fragments thereof, as disclosed herein is said to be 'specific for a first target antigen of interest as opposed to a second target antigen of interest' when it binds to the first target antigen of interest with an affinity that is at least 5 times, such as at least 10 times, such as at least 100 times, and preferably at least 1000 times higher than the affinity with which that amino acid sequence as disclosed herein binds to the second target antigen of interest. Accordingly, in certain embodiments, when an amino acid sequence as disclosed herein is said to be 'specific for' a first target antigen of interest as opposed to a second target antigen of interest, it may specifically bind to (as defined herein) the first target antigen of interest, but not to the second target antigen of interest.

The 'specificity' of an amino acid sequence, in particular an antibody fragment, such as a $V_{HH}$, or functional fragments thereof as disclosed herein can be determined based on affinity and/or avidity. The 'affinity' of an amino acid sequence as disclosed herein is represented by the equilibrium constant for the dissociation of the amino acid sequence as disclosed herein and the target protein of interest to which it binds. The lower the KD value, the stronger the binding strength between the amino acid sequence as disclosed herein and the target protein of interest to which it binds. Alternatively, the affinity can also be expressed in terms of the affinity constant (KA), which corresponds to 1/KD. The binding affinity of an amino acid sequence as disclosed herein can be determined in a manner known to the skilled person, depending on the specific target protein of interest.

The 'avidity' of an amino acid sequence as disclosed herein is the measure of the strength of binding between the amino acid sequence as disclosed herein and the pertinent target protein of interest. Avidity is related to both the affinity between a binding site on the target protein of interest and a binding site on the amino acid sequence as disclosed herein and the number of pertinent binding sites present on the amino acid sequence as disclosed herein. Typically, the amino acid sequences as disclosed herein will bind to a target protein of interest with a dissociation constant (KD) of less than about 1 micromolar (1 μM), and preferably less than about 1 nanomolar (1 nM) [i.e., with an association constant (KA) of about 1,000,000 per molar ($10^6$ $M^{-1}$, 1E6 /M) or more and preferably about 1,000,000,000 per molar ($10^9$ $M^{-1}$, 1E9 /M) or more]. A KD value greater than about 1 millimolar is generally considered to indicate non-binding or non-specific binding. It is generally known in the art that the KD can also be expressed as the ratio of the dissociation rate constant of a complex, denoted as kOff (expressed in seconds$^{-1}$ or s$^{-1}$), to the rate constant of its association, denoted kOn (expressed in molar$^{-1}$ seconds$^{-1}$ or $M^{-1}$ s$^{-1}$). In particular, an amino acid sequence as disclosed herein will bind to the target protein of interest with a kOff ranging between 0.1 and 0.0001s$^{-1}$ and/or a kOn ranging between 1,000 and 1,000,000 $M^{-1}$ s$^{-1}$. Binding affinities, kOff and kOn rates may be determined by means of methods known to the person skilled in the art, for example ELISA methods, isothermal titration calorimetry, surface plasmon resonance, fluorescence-activated cell sorting analysis, and the more.

An amino acid sequence, in particular an antibody fragment, such as a $V_{HH}$, as disclosed herein is considered to be '(in) essentially isolated (form)' as used herein, when it has been extracted or purified from the host cell and/or medium in which it is produced.

In respect of the amino acid sequences, in particular antibody fragments, such as a $V_{HH}$'s or functional fragments thereof, as disclosed herein, the terms 'binding region', 'binding site' or 'interaction site' present on the amino acid sequences as disclosed herein shall herein have the meaning of a particular site, part, domain or stretch of amino acid residues present on the amino acid sequence as disclosed herein that is responsible for binding to a target molecule. Such binding region essentially consists of specific amino acid residues from the amino acid sequence as disclosed herein which are in contact with the target molecule.

The 'half-life' of an amino acid sequence, in particular an antibody fragment, such as a $V_{HH}$ or functional fragments thereof, as disclosed herein can generally be defined as the time that is needed for the in vivo serum concentration of the amino acid sequence as disclosed herein to be reduced by 50%. The in vivo half-life of an amino acid sequence as disclosed herein can be determined in any manner known to the person skilled in the art, such as by pharmacokinetic analysis. As will be clear to the skilled person, the half-life can be expressed using parameters such as the t1/2-alpha, t1/2-beta and the area under the curve (AUC). An increased half-life in vivo is generally characterized by an increase in one or more and preferably in all three of the parameters t1/2-alpha, t1/2-beta and the area under the curve (AUC).

Aptamers that bind specifically to the biomarker of the invention can be obtained using the so called SELEX or Systematic Evolution of Ligands by EXponential enrichment. In this system, multiple rounds of selection and amplification can be used to select for DNA or RNA molecules with high specificity for a target of choice, developed by Larry Gold and coworkers and described in U.S. Pat. No. 6,329,145. Recently a more refined method of designing co-called photoaptamers with even higher specificity has been described in U.S. Pat. No. 6,458,539 by the group of Larry Gold.

Methods of identifying binding agents such as interacting proteins and small molecules are also known in the art. Examples are two-hybrid analysis, immunoprecipitation methods and the like.

In addition, the invention also provides tools and methods for the identification of binding molecules, such as peptides or small molecules, monoclonal- or polyclonal antibodies, nanobodies, affibodies, minibodies, diabodies, single chain antibodies, antibody fragments, aptamers, photoaptamers, lipocalins, specifically interacting small molecules, Molecular Imprinting Polymers (MIPs), DARPins, ankyrins, specifically interacting proteins or peptides, and other molecules that specifically bind to the biomarker, e.g. using cells or cell-lines that do or do not express DPP6-K.

To this end, the invention provides several cells and/or cell-lines (rodent pancreatic islets, rat INS-1E, cells and the human beta cell line EndoC-BH1) that are DPP6-K positive and two cell-lines (human PANC-1 and CAPAN-2 cells) that are DPP6-K negative. These cells or cell-lines can be used to screen for binding agents or compounds that specifically bind to cells positive for DPP6-K, but not to cells negative for DPP6-K in order to identify new tracer molecules for visualization of beta-cells e.g. in PET, PET-CT or SPECT analysis.

The invention further provides methods for preparing or generating $V_{HH}$ domain sequences or functional fragments thereof specifically binding to the extracellular domain of DPP6-K, as well as methods for producing nucleic acids encoding these and host cells, products and compositions comprising these heavy chain variable domain sequences. Some preferred but non-limiting examples of such methods will become clear from the further description herein.

As will be clear to the skilled person, one particularly useful method for preparing heavy chain variable domain sequences as disclosed herein generally comprises the steps of:

(a) expressing a nucleotide sequence encoding a heavy chain variable domain sequence as disclosed herein or a vector or genetic construct a nucleotide sequence encoding that heavy chain variable domain sequence and (b) optionally isolating and/or purifying the heavy chain variable domain sequence.

In particular embodiments envisaged herein, the heavy chain variable domain sequences specifically binding to the extracellular domain of DPP6-K can be obtained by methods which involve generating a random library of $V_{HH}$ sequences and screening this library for an $V_{HH}$ sequence capable of specifically binding to the extracellular domain of DPP6-K.

Accordingly, in particular embodiments, methods for preparing a heavy chain variable domain sequence as disclosed herein comprise the steps of
a) providing a set, collection or library of amino acid sequences of $V_{HH}$ domains; and
b) screening said set, collection or library of $V_{HH}$ domains for amino acid sequences that can bind to and/or have affinity for the extracellular domain of DPP6-K.
and
c) isolating the $V_{HH}$ domains that can bind to and/or have affinity for the extracellular domain of DPP6-K.

In such a method, the set, collection or library of $V_{HH}$ sequences may be any suitable set, collection or library of amino acid sequences. For example, the set, collection or library of $V_{HH}$s sequences may be a set, collection or library of immunoglobulin fragment sequences (as described herein), such as a naïve set, collection or library of immunoglobulin fragment sequences; a synthetic or semi-synthetic set, collection or library of immunoglobulin fragment sequences; and/or a set, collection or library of immunoglobulin fragment sequences that have been subjected to affinity maturation.

In particular embodiments of this method, the set, collection or library of $V_{HH}$ sequences may be an immune set, collection or library of immunoglobulin fragment sequences, for example derived from a mammal that has been suitably immunized with the extracellular domain of DPP6 or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the above methods, the set, collection or library of $V_{HH}$ sequences may be displayed on a phage, phagemid, ribosome or suitable micro-organism (such as yeast), such as to facilitate screening. Suitable methods, techniques and host organisms for displaying and screening (a set, collection or library of) amino acid sequences will be clear to the person skilled in the art, for example on the basis of the further disclosure herein. Reference is also made to the review by Hoogenboom in Nature Biotechnology, 23, 9, 1105-1116 (2005).

In other embodiments, the methods for generating the heavy chain variable domain sequences as disclosed herein comprises at least the steps of:
a) providing a collection or sample of cells expressing $V_{HH}$ domain amino acid sequences;
b) screening said collection or sample of cells for cells that express a $V_{HH}$ amino acid sequence that can bind to and/or have affinity for the extracellular domain of DPP6-K;
and
c) either (i) isolating said amino acid sequence; or (ii) isolating from said cell a nucleic acid sequence that encodes said amino acid sequence, followed by expressing said amino acid sequence.

The collection or sample of cells may for example be a collection or sample of B-cells. Also, in this method, the sample of cells may be derived from a mammal that has been suitably immunized with the extracellular domain of DPP6or with a suitable antigenic determinant based thereon or derived therefrom, such as an antigenic part, fragment, region, domain, loop or other epitope thereof. In one particular embodiment, the antigenic determinant may be an extracellular part, region, domain, loop or other extracellular epitope(s).

In other embodiments, the method for generating a heavy chain variable domain sequence specifically binding to the extracellular domain of DPP6-K, may comprise at least the steps of:
a) providing a set, collection or library of nucleic acid sequences encoding a $V_{HH}$ domain amino acid sequence;
b) screening said set, collection or library of nucleic acid sequences for nucleic acid sequences that encode a $V_{HH}$ amino acid sequence that can bind to and/or has affinity for the extracellular domain of DPP6-K;
and
c) isolating said nucleic acid sequence, followed by expressing said amino acid sequence.

In the above methods, the set, collection or library of nucleic acid sequences encoding amino acid sequences may for example be a set, collection or library of nucleic acid sequences encoding a naïve set, collection or library of immunoglobulin fragment sequences; a set, collection or library of nucleic acid sequences encoding a synthetic or semi-synthetic set, collection or library of immunoglobulin fragment sequences; and/or a set, collection or library of nucleic acid sequences encoding a set, collection or library of immunoglobulin fragment sequences that have been subjected to affinity maturation.

In particular, in such a method, the set, collection or library of nucleic acid sequences encodes a set, collection or library of $V_{HH}$ domains specifically binding to the extracellular domain of DPP6-K.

In the above methods, the set, collection or library of nucleotide sequences may be displayed on a phage, phagemid, ribosome or suitable micro-organism (such as yeast), such as to facilitate screening. Suitable methods, techniques and host organisms for displaying and screening (a set, collection or library of) nucleotide sequences encoding amino acid sequences will be clear to the person skilled in the art, for example on the basis of the further disclosure herein. Reference is also made to the review by Hoogenboom in Nature Biotechnology, 23, 9, 1105-1116 (2005).

The invention also relates to $V_{HH}$ sequences that are obtainable or obtained by the above methods, or alternatively by a method that comprises one of the above methods and in addition at least the steps of determining the nucleotide sequence or amino acid sequence of said $V_{HH}$ sequence; and of expressing or synthesizing said $V_{HH}$ sequence in a manner known per se, such as by expression in a suitable host cell or host organism or by chemical synthesis.

In some cases, the methods for producing the $V_{HH}$ amino acid sequences binding specifically to the extracellular domain of DPP6-K as envisaged herein may further comprise the step of isolating from the amino acid sequence library at least one $V_{HH}$ domain having detectable binding affinity for, or detectable in vitro effect on DPP6-K.

These methods may further comprise the step of amplifying a sequence encoding at least one $V_{HH}$ domain having detectable binding affinity for, or detectable in vitro effect on the activity of DPP6-K. For example, a phage clone displaying a particular amino acid sequence, obtained from a selection step of a method described herein, may be amplified by reinfection of a host bacteria and incubation in a growth medium.

In particular embodiments, these methods may encompass determining the sequence of the one or more amino acid sequences capable of binding to the extracellular domain of DPP6-K.

Where a heavy chain variable domain sequence, comprised in a set, collection or library of amino acid sequences, is displayed on a suitable cell or phage or particle, it is possible to isolate from said cell or phage or particle, the nucleotide sequence that encodes that amino acid sequence. In this way, the nucleotide sequence of the selected amino acid sequence library member(s) can be determined by a routine sequencing method.

In further particular embodiments, the methods for producing a $V_{HH}$ domain as envisaged herein comprise the step of expressing said nucleotide sequence(s) in a host organism under suitable conditions, so as to obtain the actual desired amino acid sequence. This step can be performed by methods known to the person skilled in the art.

In addition, the obtained $V_{HH}$ domain sequences having detectable binding affinity for, or detectable in vitro effect on the activity of DPP6-K, may be synthesized as soluble protein construct, optionally after their sequence has been identified.

For instance, the $V_{HH}$ domain sequences obtained, obtainable or selected by the above methods can be synthesized using recombinant or chemical synthesis methods known in the art. Also, the amino acid sequences obtained, obtainable or selected by the above methods can be produced by genetic engineering techniques. Thus, methods for synthesizing the $V_{HH}$ sequences obtained, obtainable or selected by the above methods may comprise transforming or infecting a host cell with a nucleic acid or a vector encoding an amino acid sequence having detectable binding affinity for, or detectable in vitro effect on the activity of DPP6-K. Accordingly, the $V_{HH}$ sequences having detectable binding affinity for, or detectable in vitro effect on the activity of DPP6-K can be made by recombinant DNA methods. DNA encoding the amino acid sequences can be readily synthesized using conventional procedures. Once prepared, the DNA can be introduced into expression vectors, which can then be transformed or transfected into host cells such as *E. coli* or any suitable expression system, in order to obtain the expression of amino acid sequences in the recombinant host cells and/or in the medium in which these recombinant host cells reside.

It should be understood, as known by someone skilled in the art of protein expression and purification, that the $V_{HH}$ domain produced from an expression vector using a suitable expression system may be tagged (typically at the N-terminal or C-terminal end of the amino acid sequence) with e.g. a His-tag or other sequence tag for easy purification.

Transformation or transfection of nucleic acids or vectors into host cells may be accomplished by a variety of means known to the person skilled in the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

Suitable host cells for the expression of the desired heavy chain variable domain sequences may be any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic plant.

Thus, the application also provides methods for the production of $V_{HH}$ domain sequences having detectable binding affinity for, or detectable in vitro effect on the activity of DPP6-K comprising transforming, transfecting or infecting a host cell with nucleic acid sequences or vectors encoding such $V_{HH}$ sequences and expressing their amino acid sequences under suitable conditions.

In yet another embodiment, the invention further provides methods for the manufacture (or the production of which is equivalent wording) a pharmaceutical composition as disclosed herein.

In particular embodiments, the invention provides methods for producing a pharmaceutical composition as disclosed herein, at least comprising the steps of:
obtaining at least one $V_{HH}$ or a functional fragment thereof, which specifically binds to DPP6-K, and
formulating said $V_{HH}$ or functional fragment thereof in a pharmaceutical composition.

In particular embodiments of these methods, the step of obtaining at least one heavy chain variable domain or functional fragment thereof, which specifically binds to DPP6-K comprises:
(a) expressing a nucleotide sequence encoding a $V_{HH}$ or functional fragment thereof, which specifically binds to DPP6-K, and optionally
(b) isolating and/or purifying the $V_{HH}$ or functional fragment thereof.

In other particular embodiments of these methods, the step of obtaining at least one $V_{HH}$ or functional fragment thereof, which specifically binds to DPP6-K comprises:
a) providing a set, collection or library of $V_{HH}$ domain sequences or functional fragments of $V_{HH}$ sequences;
b) screening said set, collection or library of $V_{HH}$ domain sequences or sequences of functional fragments thereof for sequences that specifically bind to and/or have affinity for DPP6-K, and
c) optionally isolating the $V_{HH}$ sequences or sequences of functional fragments thereof that specifically bind to and/or have affinity for DPP6-K.

In certain aspects, the $V_{HH}$ domains or functional fragments thereof specifically binding to DPP6-K as disclosed herein may be optionally linked to one or more further groups, moieties, or residues via one or more linkers. These one or more further groups, moieties or residues can serve for binding to other targets of interest. It should be clear that such further groups, residues, moieties and/or binding sites may or may not provide further functionality to the heavy chain variable domains as disclosed herein and may or may not modify the properties of the heavy chain variable domain as disclosed herein. Such groups, residues, moieties or binding units may also for example be chemical groups which can be biologically active.

These groups, moieties or residues are, in particular embodiments, linked N- or C-terminally to the heavy chain variable domain, in particularly C-terminally linked.

In particular embodiments, the $V_{HH}$ domains or functional fragments thereof specifically binding to DPP6-K as disclosed herein may also have been chemically modified. For example, such a modification may involve the introduction or linkage of one or more functional groups, residues or moieties into or onto the heavy chain variable domain.

These groups, residues or moieties may confer one or more desired properties or functionalities to the heavy chain variable domain. Examples of such functional groups will be clear to the skilled person.

For example, the introduction or linkage of such functional groups to a heavy chain variable domain can result in an increase in the solubility and/or the stability of the heavy chain variable domain, in a reduction of the toxicity of the heavy chain variable domain, or in the elimination or attenuation of any undesirable side effects of the heavy chain variable domain, and/or in other advantageous properties.

In particular embodiments, the one or more groups, residues, moieties are linked to the heavy chain variable domain via one or more suitable linkers or spacers.

While the $V_{HH}$ domains specifically binding to DPP6-K as disclosed herein are preferably in monomeric form (as further described herein), in particular alternative embodiments, two or more of the $V_{HH}$ domains or functional fragments thereof, specifically binding to DPP6-K as disclosed herein may be linked to each other or may be interconnected. In particular embodiments, the two or more heavy chain variable domains or functional fragments thereof are linked to each other via one or more suitable linkers or spacers. Suitable spacers or linkers for use in the coupling of different heavy chain variable domains as disclosed herein will be clear to the skilled person and may generally be any linker or spacer used in the art to link peptides and/or proteins.

Some particularly suitable linkers or spacers include for example, but are not limited to, polypeptide linkers such as glycine linkers, serine linkers, mixed glycine/serine linkers, glycine- and serine-rich linkers or linkers composed of largely polar polypeptide fragments, or homo- or heterobifunctional chemical crosslinking compounds such as glutaraldehyde or, optionally PEG-spaced, maleimides or NHS esters.

For example, a polypeptide linker or spacer may be a suitable amino acid sequence having a length between 1 and 50 amino acids, such as between 1 and 30, and in particular between 1 and 10 amino acid residues. It should be clear that the length, the degree of flexibility and/or other properties of the linker(s) may have some influence on the properties of the heavy chain variable domains, including but not limited to the affinity, specificity or avidity for the fungal target. It should be clear that when two or more linkers are used, these linkers may be the same or different. In the context and disclosure of the present invention, the person skilled in the art will be able to determine the optimal linkers for the purpose of coupling heavy chain variable domains as disclosed herein without any undue experimental burden.

The present invention also encompasses parts, fragments, analogs, mutants, variants, and/or derivatives of the radiolabelled $V_{HH}$ domains specifically binding to of DPP6-K as disclosed herein and/or polypeptides comprising or essentially consisting of one or more of such parts, fragments, analogs, mutants, variants, and/or derivatives, as long as these parts, fragments, analogs, mutants, variants, and/or derivatives are suitable for the purposes envisaged herein.

Such parts, fragments, analogs, mutants, variants, and/or derivatives according to the invention are still capable of specifically binding to DPP6-K.

For example, the invention provides a number of stretches of amino acid residues (i.e. small peptides), also referred to herein as CDR sequences of the $V_{HH}$'s as disclosed herein, that are particularly suited for binding to DPP6-K. These stretches may be regarded as being functional fragments of the $V_{HH}$'s as disclosed herein and may be present in, and/or may be incorporated into any suitable scaffold (protein), such as but not limited to the $V_{HH}$'s as disclosed herein, in particular in such a way that they form (part of) the antigen binding site of that suitable scaffold or $V_{HH}$. It should however be noted that the invention in its broadest sense is not limited to a specific structural role or function that these stretches of amino acid residues may have in the scaffolds or $V_{HH}$'s as disclosed herein, as long as these stretches of amino acid residues allow these scaffolds or $V_{HH}$'s as disclosed herein to specifically bind to DPP6-K.

In a further aspect, the present invention provides nucleic acid sequences encoding the $V_{HH}$ domain amino acid sequences in the compositions as disclosed herein (or suitable fragments thereof). These nucleic acid sequences can also be in the form of a vector or a genetic construct or polynucleotide. The nucleic acid sequences as disclosed herein may be synthetic or semi-synthetic sequences, nucleotide sequences that have been isolated from a library (and in particular, an expression library), nucleotide sequences that have been prepared by PCR using overlapping primers, or nucleotide sequences that have been prepared using techniques for DNA synthesis known per se.

The genetic constructs as disclosed herein may be DNA or RNA, and are preferably double-stranded DNA. The genetic constructs of the invention may also be in a form suitable for transformation of the intended host cell or host organism in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e., a vector that can provide for expression in vitro and/or in vivo (e.g. in a suitable host cell, host organism and/or expression system).

Accordingly, in another further aspect, the present invention also provides vectors comprising one or more nucleic acid sequences as disclosed herein.

In still a further aspect, the present invention provides hosts or host cells that express or are capable of expressing one or more amino acid sequences as disclosed herein. Suitable examples of hosts or host cells for expression of the $V_{HH}$ sequences, polypeptides of the invention will be clear to the skilled person.

In a further aspect, the present invention provides polypeptides (also referred to herein as "polypeptides as disclosed herein") that comprise or essentially consist of at least one $V_{HH}$ sequence of the present invention that specifically binds to DPP6-K. The polypeptides of the invention may comprise at least one $V_{HH}$ or functional fragments thereof as disclosed herein and optionally one or more further groups, moieties, residues optionally linked via one or more linkers.

In particularly preferred embodiments, the present invention provides polypeptides and pharmaceutical compositions comprising a $V_{HH}$ domain in its monomeric form, i.e. comprising only one $V_{HH}$ domain so as to minimize the in vivo half-life of said polypeptides and pharmaceutical compositions as much as possible.

In alternative embodiments, however the present invention also provides polypeptides and pharmaceutical compositions comprising two or more identical or different $V_{HH}$ domains resulting in a bivalent (or multivalent) or a bispecific or (multispecific) polypeptide.

The polypeptides as disclosed herein may at least contain one or more further groups, moieties or residues for binding to other targets or target proteins of interest. It should be clear that such further groups, residues, moieties and/or binding sites may or may not provide further functionality to the amino acid sequences as disclosed herein (and/or to the polypeptide or composition in which it is present) and may or may not modify the properties of the amino acid sequence as disclosed herein. Such groups, residues, moieties or binding units may also for example be chemical groups which can be biologically and/or pharmacologically active.

These groups, moieties or residues are, in particular embodiments, linked N- or C-terminally to the amino acid sequence as disclosed herein.

It should be noted that the invention is not limited as to the origin of the $V_{HH}$ sequences or functional fragments thereof, polypeptides or compositions of the invention (or of the nucleotide sequences of the invention used to express them). Furthermore, the present invention is also not limited as to the way that the $V_{HH}$ sequences, polypeptides or nucleotide sequences as disclosed herein have been generated or obtained. Thus, the amino acid sequences as disclosed herein may be synthetic or semi-synthetic amino acid sequences, polypeptides or proteins.

The amino acid sequences, polypeptides and compositions provided by the invention can be in essentially isolated form (as defined herein), or alternatively can form part of a polypeptide or composition as disclosed herein, which may comprise or essentially consist of at least one amino acid sequence as disclosed herein and which may optionally further comprise one or more other groups, moieties or residues (all optionally linked via one or more suitable linkers).

In one such aspect, the invention provides a method for identifying new tracer molecules that specifically bind DPP6-K positive cells comprising the steps of:

a) contacting the candidate tracer molecule with a cell-type or cell-line positive for DPP6-K and measure the interaction between the candidate tracer molecule and the cells;

b) contacting the candidate tracer molecule with a cell-type or cell-line negative for DPP6-K and measure the interaction between the candidate tracer molecule and the cells;

c) wherein these candidate tracer molecules that bind the cells of step a) but not the cells of step b) are retained as beta-cell-mass tracer molecules. In a preferred embodiment of said method, the cell-type or cell-line positive for DPP6-K is selected from the group comprising: rodent pancreatic islets, rat INS-1E cells and the human beta cell line EndoC-BH1; and the cell-type or cell-line negative for DPP6-K are PANC-1 or CAPAN-2.

The invention further provides kits for identifying new tracer molecules that specifically bind DPP6-K positive cells comprising two cell types or cell-lines, one being a cell-type or cell-line positive for DPP6-K and one being a cell-type or cell-line negative for DPP6-K. In a preferred embodiment, the DPP6-K positive cell-type or cell-line is selected from the group comprising: rodent pancreatic islets, rat INS-1E cells and the human beta cell line EndoC-BH1; and the DPP6-K negative cell-types or cell-lines are PANC-1 or CAPAN-2.

In addition to the use of cell-lines, biochemical binding assays known in the art using the DPP6-K biomarker as a target can also be used.

The term "label" includes all suitable isotopic labels for use in PET, PET-CT or SPECT analysis, labels suitable for specific extraction such as magnetic or paramagnetic beads, labels suitable for diagnosis in vitro such as fluorescent dyes or other luminescent labels, known in the art.

The term "beta cell related disorder" described in the methods or uses or kits of the invention encompasses all disorders related to beta cells such as: type 1 diabetes mellitus (T1D), type 2 diabetes mellitus (T2D), hyperinsulinemia, obesity, neuroendocrine tumors or occurrence of insulinoma.

Additionally, the biomarker of the invention can also be used in in-vitro methods for the analysis of the amount or characteristics of beta cells in a cell culture, either obtained from a biopsy or from a cell-line derived culture. Beta cell specific markers of the invention can further be used to characterize the differentiation state of cells such as modified stem cells, differentiated in vitro as beta cells.

The invention further provides a method for in vivo diagnosis of beta cell deficiency in a subject comprising the steps of:

a) creating an expression matrix by constructing features on a computer from in vivo measurements obtained from a reference pool of healthy subjects, wherein the expression matrix comprises the expression data of the DPP6-K biomarker;

b) storing the expression data of the DPP6-Kin said reference pool;

c) determining the in vivo expression of DPP6-K in the pancreas of the subject to be diagnosed;

d) comparing the expression data obtained in step c) with the expression data obtained in step (b)

e) determining whether there is a deviation of the DPP6-K expression in the subject to be diagnosed, compared to the expression of DPP6-K in the reference pool of healthy subjects, wherein a decrease in DPP6-K expression in the subject as compared to the expression in the reference pool of healthy subjects is indicative for beta cell deficiency.

The invention further provides a method for in vivo diagnosis of beta cell deficiency in a subject comprising the steps of:
a) creating an expression matrix by constructing features on a computer from in vivo measurements obtained from a reference pool of subjects having a condition related to beta cell deficiency, wherein the expression matrix comprises the expression data of the DPP6-K biomarker;
b) storing the expression data of the DPP6-K in said reference pool;
c) determining the in vivo expression of DPP6-K in the pancreas of the subject to be diagnosed;
d) comparing the expression data obtained in step c) with the expression data obtained in step (b);
e) determining whether there is a deviation of the DPP6-K expression in the subject to be diagnosed, compared to the expression of DPP6-K in the reference pool of subjects having a condition related to beta cell deficiency, wherein no deviation in DPP6-K expression in the subject as compared to the expression in the reference pool of subjects having a condition related to beta cell deficiency is indicative for said beta cell deficiency.

In a further aspect the invention relates to a system comprising:
- a computer data repository that comprises a reference value of the quantity of DPP6-K in a pool of subjects representing a known diagnosis, prediction and/or prognosis of beta cell deficiency; and
- a computer system programmed to access the data repository and to use information from the data repository in combination with information on the quantity of DPP6-K in a subject under diagnosis to make a diagnosis, prediction and/or prognosis of beta cell deficiency in said subject.

Related embodiments of the invention concern a method for making diagnosis, prediction and/or prognosis of beta cell deficiency in a subject comprising:
(i) receiving data representative of values of the in vivo pancreatic quantity of DPP6-K from a subject;
(ii) accessing a data repository on a computer, said data repository comprising a reference value of the in vivo pancreatic quantity of DPP6-K , said reference value representing a known diagnosis, prediction and/or prognosis of beta cell dysfunction; and
(iii) comparing the data as received in (i) with the reference value in the data repository on the computer, thereby making a diagnosis, prediction and/or prognosis of beta cell dysfunction in the subject.

In certain embodiments, the determination of what action is to be taken, e.g., by a clinician, in view of said diagnosis, prediction and/or prognosis is performed by a (the) computer. In certain embodiments, a (the) computer reports (i.e., generates an electronic report of) the action to be taken, preferably substantially in real time.

In certain embodiments, the invention relates to a method for treating beta cell dysfunction in a subject in need of said treatment, the method comprising the steps of:
(i) in vivo measurement of the quantity of DPP6-K in the pancreas of the subject;
(ii) comparing the quantity of DPP6-K as measured in (i) with a reference value of the quantity of DPP6-K, said reference value representing a known diagnosis, prediction and/or prognosis of beta cell dysfunction;
(iii) finding a deviation or no deviation of the quantity of DPP6-K as measured in (i) from the reference value;
(iv) attributing said finding of deviation or no deviation to a particular diagnosis, prediction and/or prognosis of beta cell dysfunction in the subject;
(v) inferring from said particular diagnosis, prediction and/or prognosis of beta cell dysfunction in the subject the presence or absence of a need for a therapeutic or prophylactic treatment of beta cell dysfunction in the subject; and
(vi) subjecting the subject to a therapeutic or prophylactic treatment of beta cell dysfunction when the subject is in need of said treatment.

Illustrative therapeutic and prophylactic treatment of beta cell dysfunction, e.g. diabetes can encompass one or more of the following: the regular administration of insulin, the physiological control of glycemia, the normalization of glycemia, to restore insulin secretion in vivo from cells. Several strategies for said in vivo restoration have been proposed: xenotransplantation of insulin-producing cells from animals, in vitro differentiation of isolated stem cells into insulin-secreting cells and re-implantation thereof in the patient or allotransplantation of isolated pancreatic islets from another subject.

The invention is illustrated by the following non-limiting examples

EXAMPLES

Example 1

Selection Strategy for the Identification of Beta Cell Specific Plasma Membrane Proteins and Validation of the Islet Specific Expression of the Selected Biomarkers Material and Methods
Ethical Statements Human pancreatic islet collection and handling were approved by the local Ethical Committee in Pisa, Italy and performed as previously described (1). Female SCID CB-17/Icr-Prkdcscid/Rj mice (Janvier labs, Le Genest-Saint-Isle, France), were used according to the rules of the Belgian regulations for animal care, with approval by the Ethical Committee for Animal Experiments of the ULB, Brussels, Belgium.

Cell Culturing, Generation of DPP6 Overexpressing Cells and Cytokine Exposure

To generate DPP6 overexpressing cells the Chinese Hamster Ovary (CHO) cells (ATCC, Manassas, USA) were selected for these experiments, as they do not express Human DPP6. CHO cells were cultured in Ham's F-12 Nutrient mix+GlutaMax, supplemented with Penicillin-Streptomycin and 5% Fetal Bovine Serum (FBS) all from (ThermoFisher Scientific, Aalst, Belgium), at 37° C., 5% $CO_2$. To induce transient DPP6 overexpression $0.8-1\times10^5$ CHO cells were transfected with a pCMV6 vector containing the HumanDPP6-001-sp3 variant, catalogue number SC310075 (Origene, Rockville, USA), construct and the transfection was confirmed by β-galactosidase staining, with 60-70% positive cells (K1465-01) (ThermoFisher Scientific). The transfection was performed overnight with Lipofectamine 2000 (2 µl/1 µg vector) in Opti-MEM media without FBS (ThermoFisher Scientific), and the media was replaced with Ham's culture medium (same as above) in the subsequent day.

Clonal human insulin-producing EndoC-βH1 cells (2) and human pancreatic islets were cultured as described previously (3). To determine if the expression of DPP6 is affected by inflammatory mediators, EndoC-βH1 cells or human pancreatic islets were exposed to recombinant human interleukin (IL)-1β (R&D Systems, Abingdon, U.K.) at 50 units/mL; and human IFN-γ (PeproTech, Rocky Hill, USA) at 1,000 units/mL for 48 hours (4).

mRNA Expression mRNA extraction, reverse transcription and quantitative PCR (qPCR) were performed as described previously (5). Briefly, poly(A)+ mRNA was isolated from 50-100 human pancreatic islets or from 1×105 EndoC-βH1 cells, using the Dynabeads mRNA DIRECT kit (ThermoFisher Scientific). qPCR amplification of Dipeptidyl-Peptidase 6 (DPP6) was performed using IQ SyBR Green Supermix on iCycler MyiQ Single Color (BIO-RAD, Hercules, USA) and compared to a standard curve; Beta-actin (ACTB) was used as a reference (housekeeping) gene. To compare the EndoC-βH1 cells and the human pancreatic islets to other tissues we used cDNA from 14 human normal tissues (BioChain, San Francisco, Calif., USA). Primers for qPCR were: Human DPP6 forward: 5'-ACAGTGAGACTGTGGAATGTTGA-3' (SEQ ID NO. 4), reverse: 5'-GAGGATCCCCATGAGGAAT-TTTG-3' (SEQ ID NO. 5), (yielding a 199 bp fragment); human actin (ACTB) forward: 5'-GCCTG-GAGAAACCTGCCAAGTATGA-3' (SEQ ID NO. 6), reverse: 5'-AACCTGGTCCTCAGTGTAGCCC-3' (SEQ ID NO. 7) (yielding a 101 bp fragment);

Western Blot

1×105 EndoC-βH1 cells were collected with Laemmli buffer, loaded on an 8% SDS-PAGE gel and transferred to a nitrocellulose membrane. Immunoblot analyses was performed after 1 hour blocking in 5% dry milk powder with a DPP6 monoclonal antibody (mAb), diluted 1:1000, ab198506 (Abcam, Cambridge, UK); alpha-Tubulin mAb, diluted 1:5000, T5168, (Sigma-Aldrich, Schnelldorf, Germany) was used as a reference protein. The secondary anti-rabbit and anti-mouse mAb-HRP (catalogue numbers: 715-036-150 and 711-036-152 (Jackson ImmunoResearch Laboratories, Inc., West Grove, USA) were used at a dilution of 1:10000, the membranes were developed with SuperSignal™ West Femto Maximum Sensitivity Substrate (ThermoFisher Scientific) and the images were acquired with Chemidoc XRS+ (BIO-RAD). Densitometric analyses were performed with Image studio Lite v5.0 (Li-Cor Biotechnology, Lincoln, USA).

Humanized Mouse Models of Beta Cells

Female SCID CB-17 mice were transplanted with human insulin-producing EndoC-βH1 cells as described (7). These mice accept well xenotransplants (8; 9); in addition to this, the SCID CB-17 lack B-cells, providing a more favorable environment for the tumor to grow (10). The SCID CB-17-EndoC-βH1 model displayed a modest decrease in their glycemic levels, and their hypoglycemia could be prevented by glucose-supplemented water (see below) for long enough to perform the imaging. At the day of inoculation, 4-6×106 EndoC-βH1 cells were seeded on a rubber toric joint (EFJM, St Lubin des Joncherets, France) with Matrigel HC (Corning, New York, USA) supplemented with MmVEGF-164 (1 ng/ml) (BioLegend, San Diego, USA). The cell-containing or empty ring (negative control for imaging; see below) were then inserted into the fascia in the biceps or quadriceps femoris muscle. The mice were also operated on the left side, where the vehicle rubber ring, with Matrigel and MmVEGF-164 but without cells, was inserted. For the surgery, the mice were anesthetized with isoflurane (AbbVie SA, Wavre, Belgium). After the procedure they received both short-term analgesic (Buprenorphine 0.1 mg/kg, Reckitt Benckiser AG, Wallisellen, Switzerland) and long-term analgesic (Acetaminophen supplemented water (3 mg/ml) (Bristol-Myers Squibb, Chaussée de La Hulpe, Belgium)) for consecutive 10 days. Random glycemia was measured with ACCU-CHEK Nano glucometer (ROCHE, Basel, Switzerland) every second week until the tumor was palpable; thereafter this was done once a week between 10 am and 2 pm. The mice received water supplemented with 20% glucose (Sigma-Aldrich) to counter the progressive hypoglycemia induced by the growing EndoC-βH1 cells. Human C-peptide was evaluated in plasma. The blood samples were collected with a heparin treated syringe from a tail cut. Human C-peptide was measured with a human Ultra-sensitive C-peptide ELISA (Mercodia AB, Uppsala, Sweden).

Statistical Analyses

Data in all experiments are presented as mean±SEM. One-way ANOVA with Bidak correction for multiple comparisons was used to analyse the differences between more than two groups. When comparing two groups, the two-tailed paired or unpaired Student's t-test was utilized, unpaired was used to test the glycemic values and HuC-peptide of the EndoC-mice. Statistical testing was performed using Graph Pad Prism 6 software (Graph Software Inc., La Jolla, USA). P-values of <_0.05 were considered as significant for all tests.

Results:

Expression of DPP6

Figure 3:
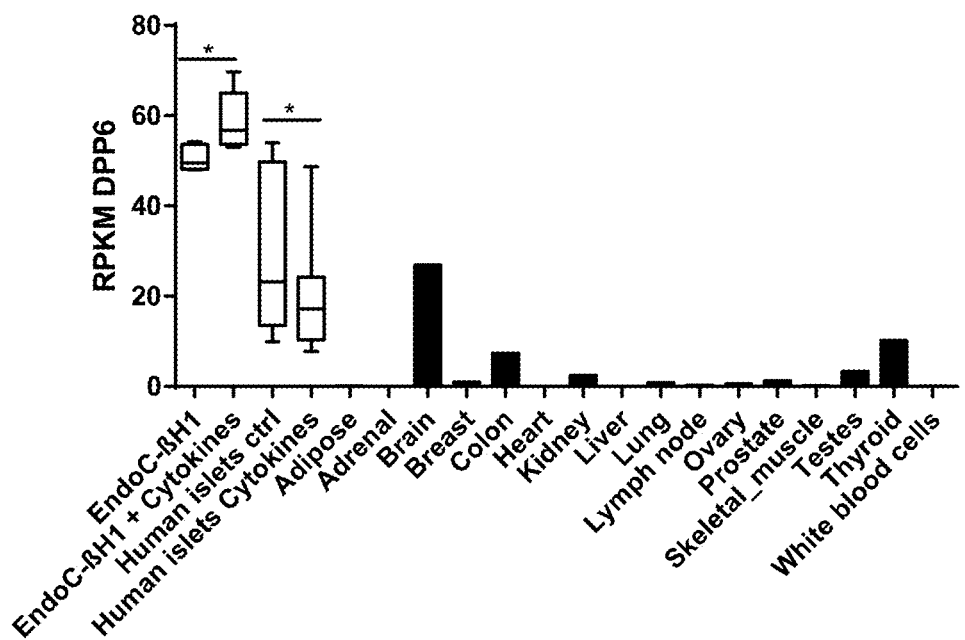
FIG. 3—Expression of DPP6 in different human tissues as evaluated by RNA sequencing. Expression of the DPP6 gene in human pancreatic islets and EndoC-βH1 cells, treated or not with cytokines (IL-1β and IFNγ), as compared to 16 other human tissues under basal condition. EndoC-βH1 with or without cytokines, n=5; human pancreatic islets with or without cytokines, n=10; all other are normal human tissues, n=1. *=p<0.05. Paired Students t-test was performed between EndoC-βH1 (with or without cytokines) and Human pancreatic islet (with or without cytokines).
Figure 4A:
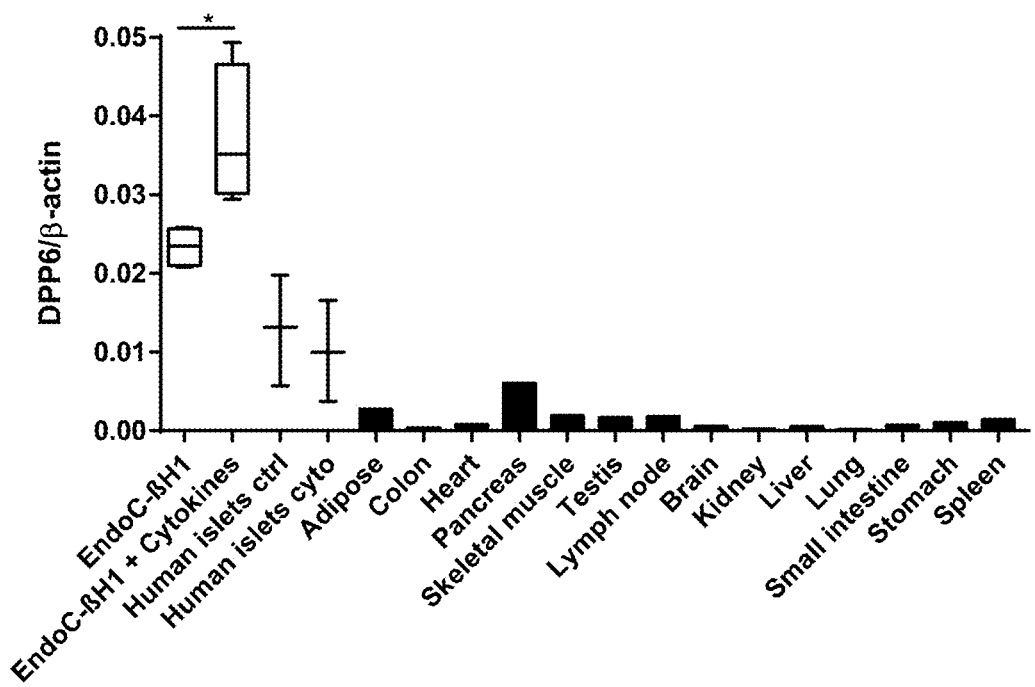
FIGS. 4A-4B—Expression of DPP6 in different human tissues.
Figure 4B:
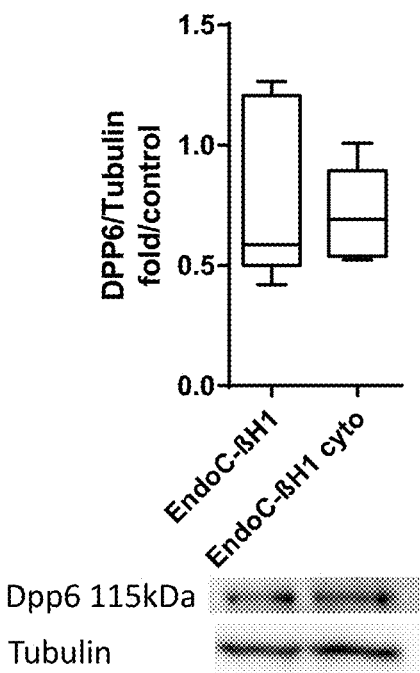
Figure 5A:
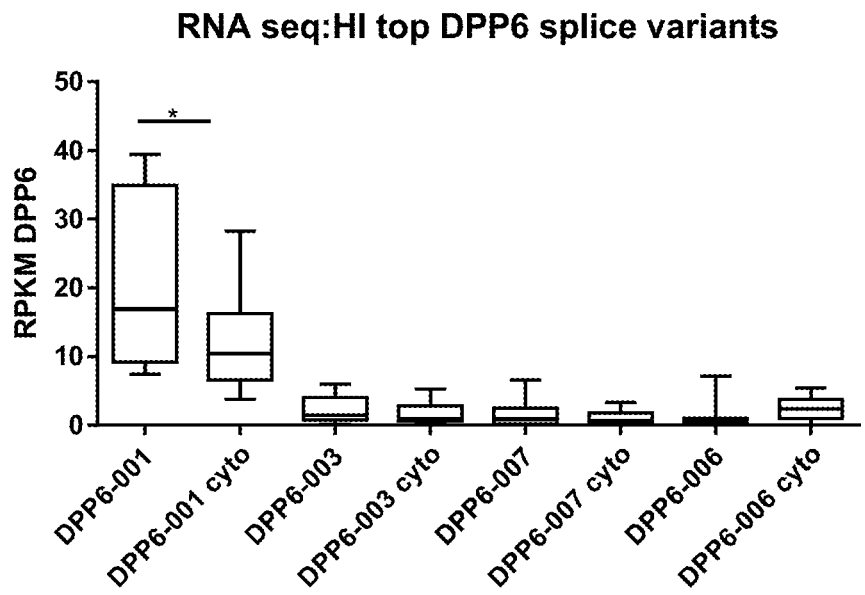
FIGS. 5A-5D—Expression of DPP6 splice variants in human pancreatic islets and in EndoC-βH1 cells. DPP6 splice variants in human pancreatic islets (n:10) and in EndoC-βH1 cells (n:5) under control (untreated) condition and after 48 h treatment with cytokines (IL1β and IFNγ).
Figure 5B:
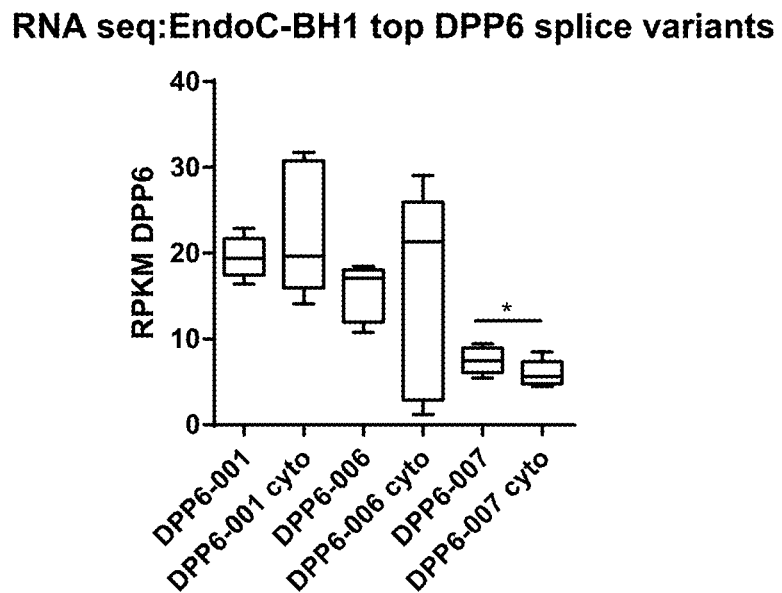
Figure 5C:
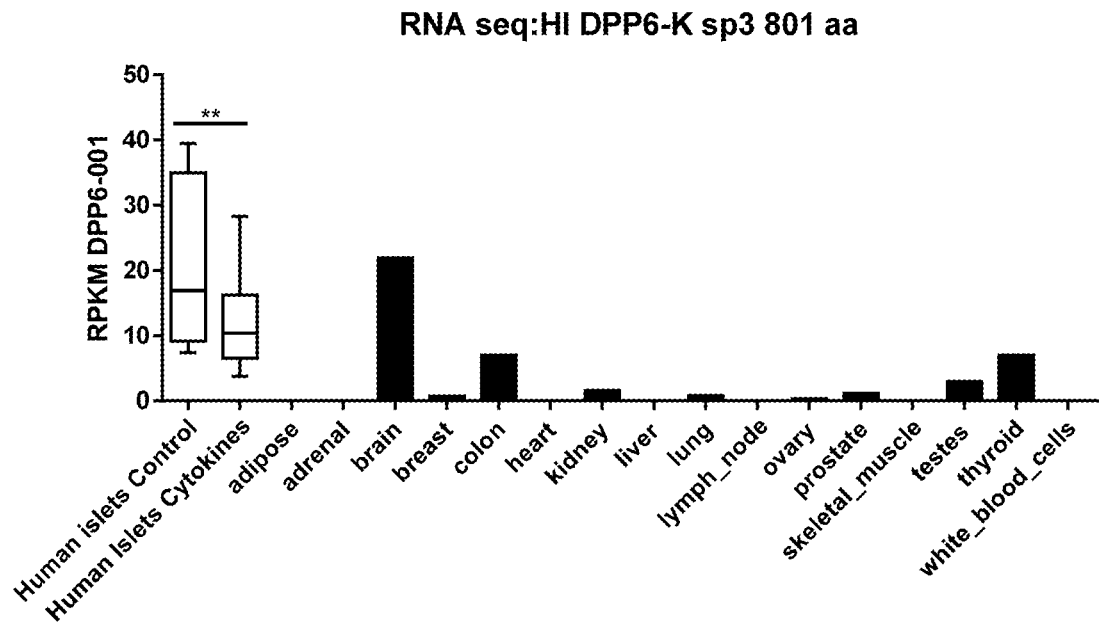
Figure 5D:
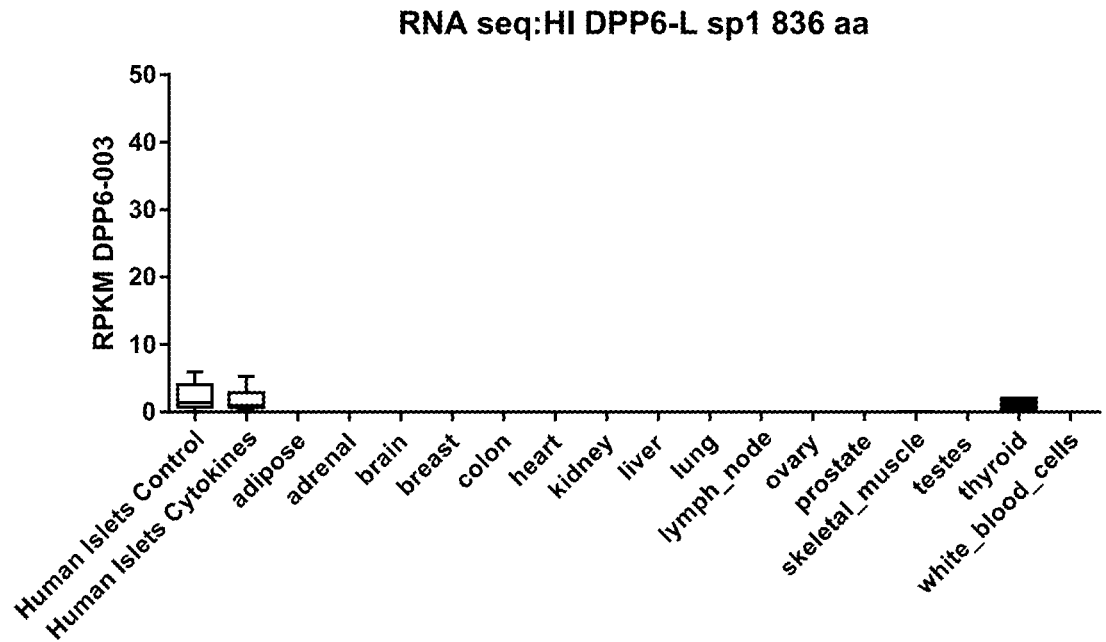

DPP6 mRNA expression was determined by qPCR in 14 different normal human tissues (FIG. 3). DPP6 had increased expression in human pancreatic islets as compared to other extra-pancreatic tissues. This is in line with the high expression level of DPP6 observed in RNA-sequenced human pancreatic islets and EndoC-βH1 cells when compared to human normal tissues ((4), Illumine Body Map 2.0 (11): GSE30611 and unpublished data) (FIG. 4). From these data it was determined that DPP6-001 (NM_001039350) (DPP6-K; DPP-6 isoform 3) is the major isoform of DPP6 expressed in EndoC-βH1 cells and human pancreatic islets (FIG. 6). DPP6 mRNA expression was up-regulated in EndoC-βH1 cells exposed to cytokines (1L-1B and IFN-γ) ($p<0.05$, n: 4) but this effect was not confirmed in human pancreatic islets (FIG. 4). Furthermore, cytokines did not modify protein expression of DPP6 in EndoC-βH1 cells (FIG. 3).

SCID CB-17/Icr-Prkdcscid/Rj (SCID-EndoC)-Endoc-BH1 Grafted Mice.

In order to validate the Nbs in vivo we created humanized mouse models that contained EndoC-βH1 cells. These cells generated palpable tumors in immunocompromised mice after 9-10 weeks, and shortly after this the mice became hypoglycemic (SCID-EndoC-βH1 mice, $p<0.001$, n=24) (FIG. 5) and human C-peptide was detectable in serum samples (SCID-EndoC-βH1 mice, $p<0.0001$, n=10-22; (FIG. 5).

Example 2

Identifying and Validating Specificity of Nanobodies Against DPP6

A recombinant extracellular domain protein (SEQ ID NO.3) was used as a source to generate nanobodies. This protein was used to immunize a dromedary, and a phage-display nanobody library from these animals was generated and biopannings were performed with said phage-displayed nanobody library and the resulting nanobodies were screened for binding to the recombinant protein.

The sequences of the nanobodies retrieved are displayed in FIG. 7 and are annotated with the IMGT numbering (international ImMunoGeneTics information system), indicating the CDRs accordingly. SEQ ID No 8 represents the heavy chain variable domain sequence and the sequence of the respective CDRs of the nanobody are defined by the sequences in the following table:

| Nb name | IMGT sequence | CDR1 sequence | CDR2 sequence | CDR3 sequence |
| --- | --- | --- | --- | --- |
| 4hD29 | SEQ ID NO. 8 | SEQ ID NO. 9 | SEQ ID NO. 10 | SEQ ID NO. 11 |

The affinity of different Nbs was analysed versus the human DPP6 protein. The best scoring nanobody was designated 4hD29 and had an affinity towards DPP6 of 1.2 $K_D$; nM.

Figure 8:
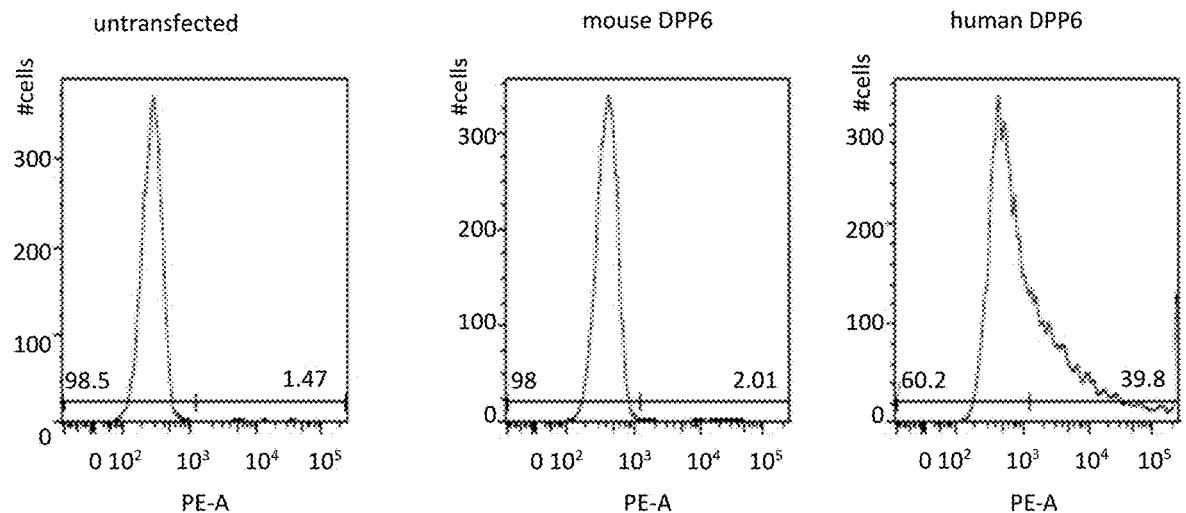
FIG. 8—Screening of antibodies for recognition of human and mouse DPP6 on transiently transfected CHO cells. Nbs were screened on cells for recognition of the mouse and human DPP6 receptor on cells. CHO cells were transiently transfected with a plasmid construct expressing either mouse or human DPP6 protein. Exemplary nanobody 4hD29 recognized human DPP6 transfected cells.

Subsequently, said Nbs were screened on cells for recognition of the mouse and human DPP6 receptor on cells. For this, CHO cells were transiently transfected with a plasmid construct expressing either human or mouse DPP6 protein (SEQ ID NO.1 or 2 respectively). Nb 4hD29 specifically recognized human DPP6 transfected cells (FIG. 8).

Figure 9:
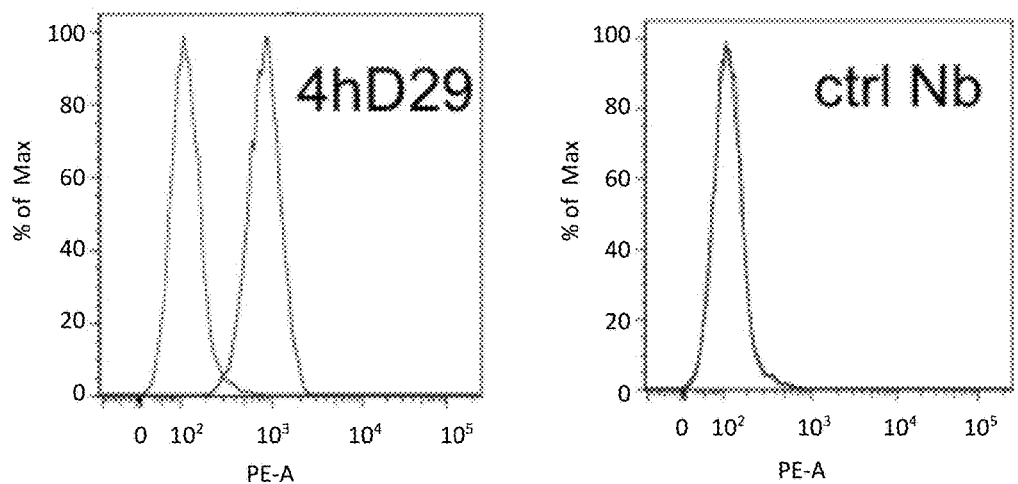
FIG. 9—Validation of nanobody recognition of DPP6 on Kelly neuroblastoma cells. Nbs were next tested for binding to human DPP6 cells that express the receptor endogenously. The human Kelly neuroblastoma cell line expresses medium levels of DPP6. 6/8 Nbs that bound to human DPP6 in transiently transfected CHO cells also recognized human DPP6 on Kelly cells. Exemplary Nb 4hD29 bound Kelly cells efficiently.

In a next step, the Nbs were tested for binding to human DPP6 cells that express the receptor endogenously. The human Kelly neuroblastoma cell line expresses medium levels of DPP6. 6 out of the 8 Nbs that bound to human DPP6 in transiently transfected CHO cells also recognized human DPP6 on Kelly cells. Nanobody 4hD29 indeed bound to Kelly cells (FIG. 9).

Figure 10:
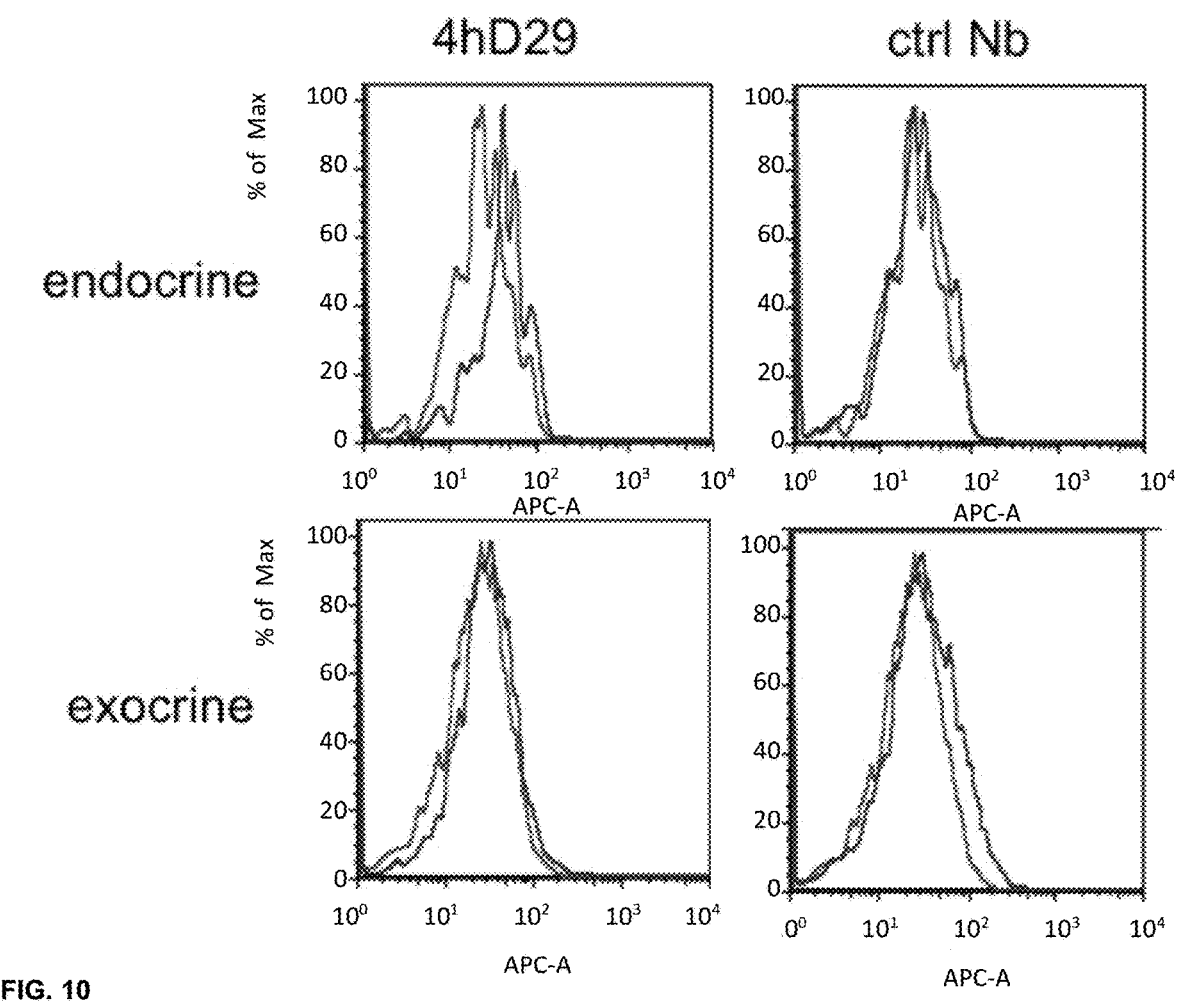
FIG. 10—FACS analysis of endocrine versus non endocrine tissue with Nb 4hD29. Nanobody 4hD29 bound more to endocrine tissue than to exocrine tissue of dissociated pancreas from a normal donor.

Subsequently, the ability of the Nbs to perform FACS analysis of endocrine versus non endocrine tissue was tested for nanobody 4hD29, which was indeed shown to bind more to endocrine tissue than to exocrine tissue of dissociated pancreas from a normal donor (FIG. 10).

Figure 11:
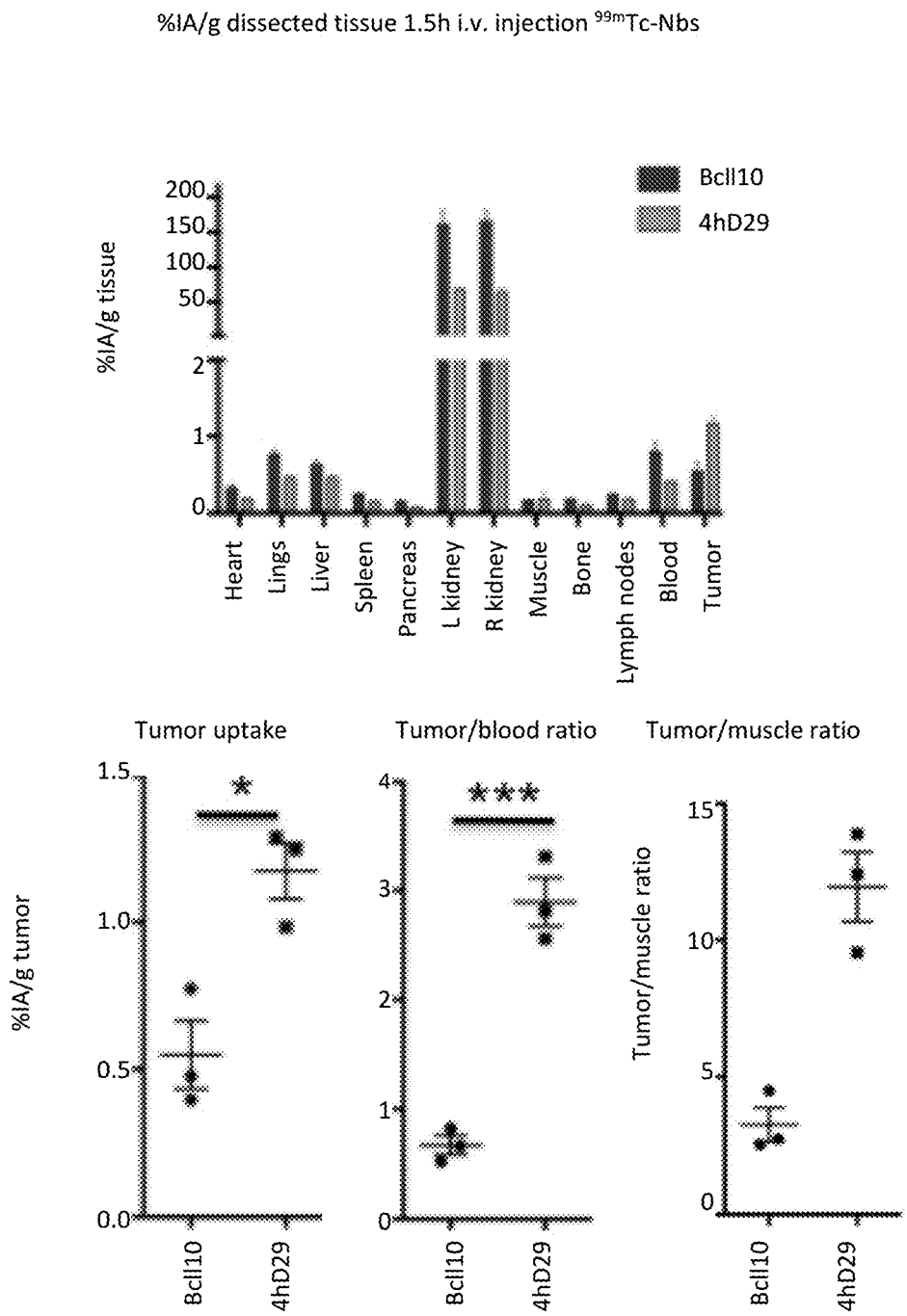
FIG. 11—Imaging studies on Kelly neuroblastoma cells in vivo. We next performed imaging studies. Human DPP6 positive Kelly neuroblastoma cells were grown subcutaneously in nude mice. 4hD29 nanobody and an irrelevant control nanobody were labeled with $^{99m}$Tc and injected i.v. in tumor-bearing mice. Mice were imaged by SPECT/CT at 1 h post-injection, and at 1.5 h postinjection mice were euthanized, dissected and radioactivity levels quantified in various organs (n=3). 4hD29 cleared fast and radioactivity signals were low in all normal organs (except kidneys which is the normal route of nanobody excretion). 4hD29 signals in all normal organs were lower as compared to the control nanobody Bcll10. In contrast, uptake in the DPP6+ Kelly tumor was higher resulting in higher tumor-to-blood and tumor-to-muscle ratios, and a clear visualization of the tumor on the images.
Figure 12:
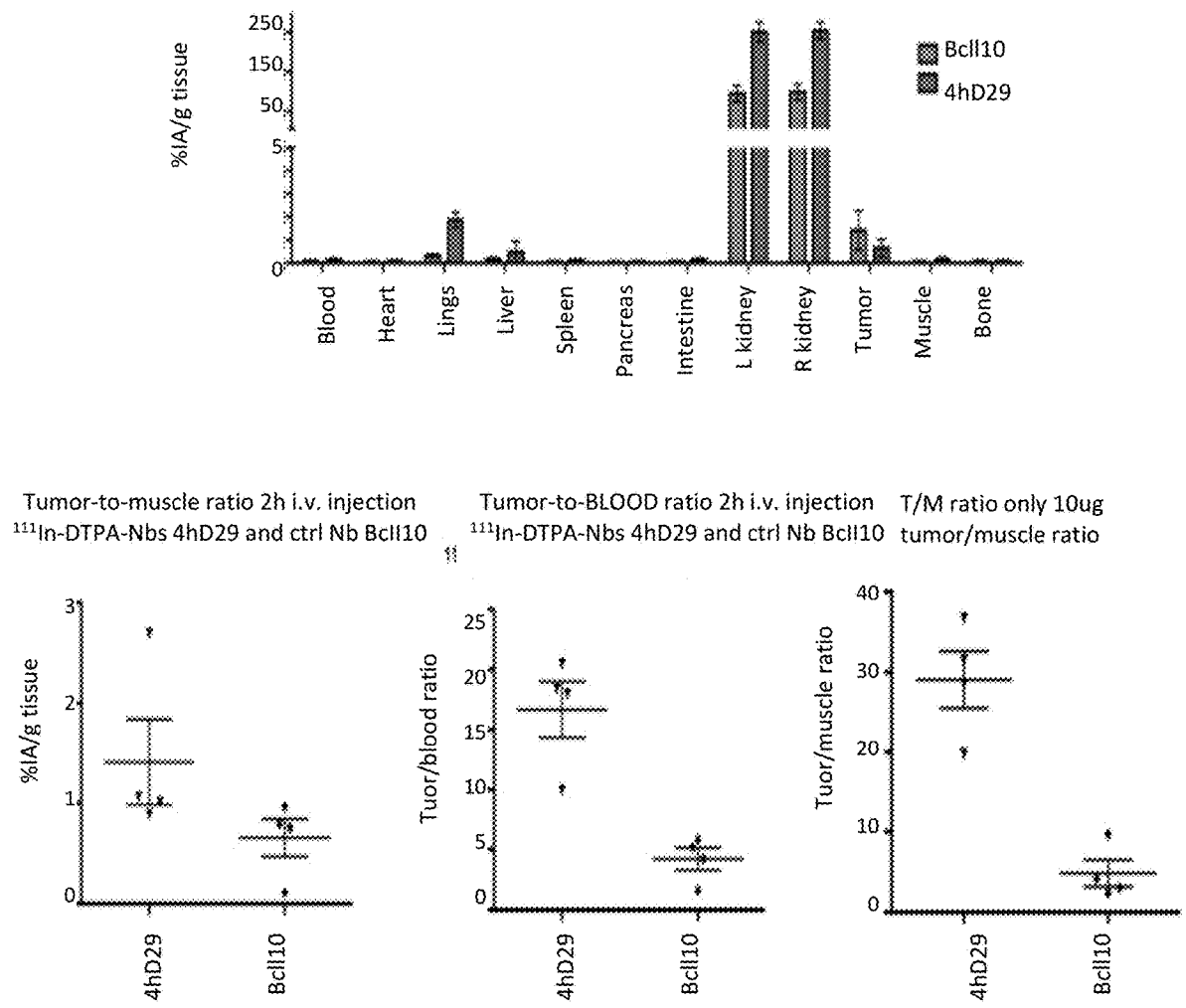
FIG. 12—Imaging studies on Kelly neuroblastoma cells in vivo. Similar results were obtained when 4hD29 and Bcll10 Nbs were labeled with $^{111}$In, and biodistribution analysis was performed at 2 h p.i.

Imaging studies were performed with Nb 4hD29 on Kelly neuroblastoma cells in vivo. Human DPP6+ Kelly neuroblastoma cells were grown subcutaneously in nude mice. 4hD29 nanobody and an irrelevant control nanobody were labeled with $^{99m}$Tc and injected i.v. in tumor-bearing mice. Mice were imaged by SPECT/CT at 1 h post-injection, and at 1.5 h postinjection mice were euthanized, dissected and radioactivity levels quantified in various organs (n=3). Nb 4hD29 cleared fast and radioactivity signals were low in all normal organs (except kidneys which is the normal route of nanobody excretion). Nb 4hD29 signals in all normal organs were lower as compared to the control nanobody Bcll10. In contrast, uptake in the DPP6+ Kelly tumor was higher resulting in higher tumor-to-blood and tumor-to-muscle ratios, and a clear visualisation of the tumor on the images was reached (FIG. 11). Similar results were obtained when 4hD29 and Bcll10 Nbs were labeled with $^{111}$In, and biodistribution analysis was performed at 2 h p.i. (FIG. 12)

Figure 13:
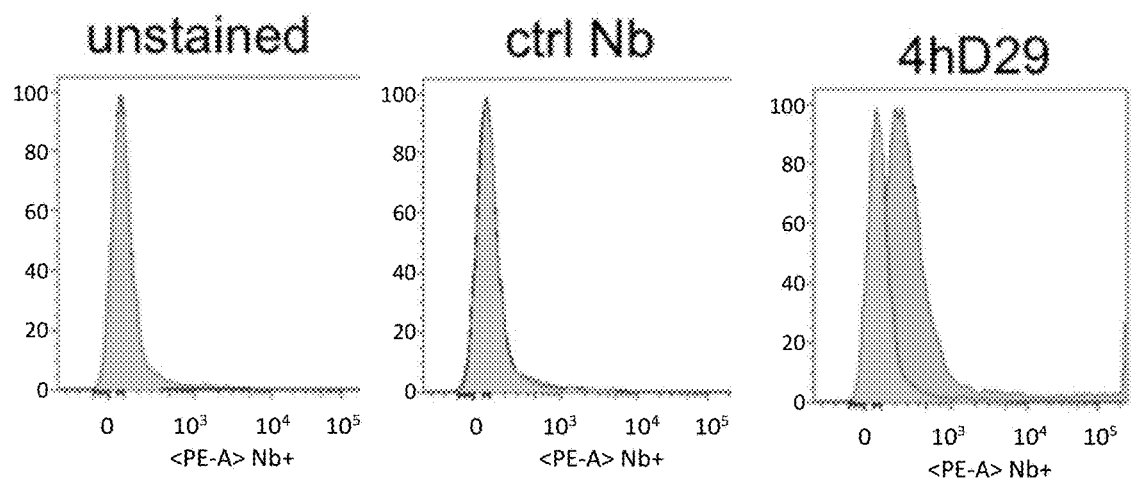
FIG. 13—FACS analysis of DPP6 Nbs on EndoC human beta cells. Next, 4hD29 and ctrl NbBcll10 were tested for binding to the Endoc-beta human beta cell line. 4hD29 specifically bound to the cells (as well as 2hD1 which was tested in parallel).

Next, FACS analysis was performed of DPP6 Nbs on EndoC human beta cells. Nb 4hD29 and ctrl NbBcll10 were tested for binding to the Endoc-beta human beta cell line. 4hD29 specifically bound to the cells (as well as 2hD1 which was tested in parallel) (FIG. 13).

Figure 14:
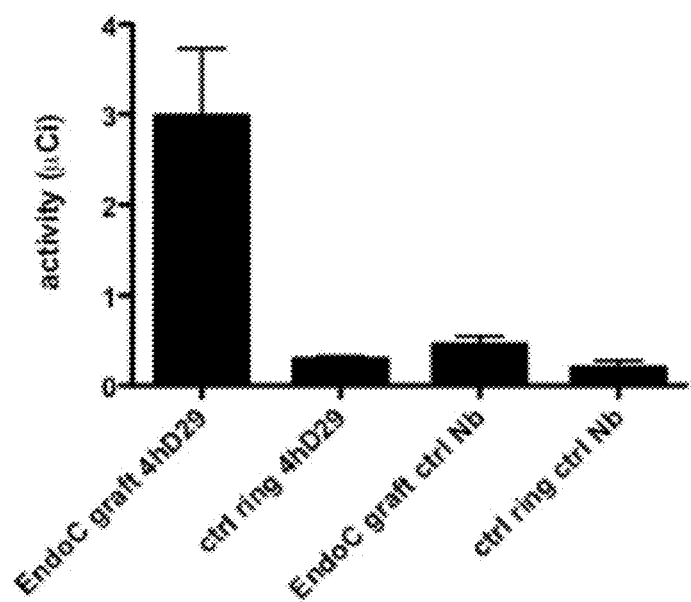
FIG. 14—in vivo analysis of DPP6 Nbs on EndoC human beta cells. Next, Endoc cells were grown in rings implanted subcutaneously in mice. Mice were injected i.v. with $^{99m}$Tc-labeled Nb 4hD29 or ctrl Nb and imaged 1 h (not shown) or 3 h p.i. Shown are the quantifications of the signals (n=2). These data clearly show that 4hD29 Nb accumulates in the Endoc graft, but not in the control ring. Ctrl Nb does not accumulate in either of them.
Figure 15A:
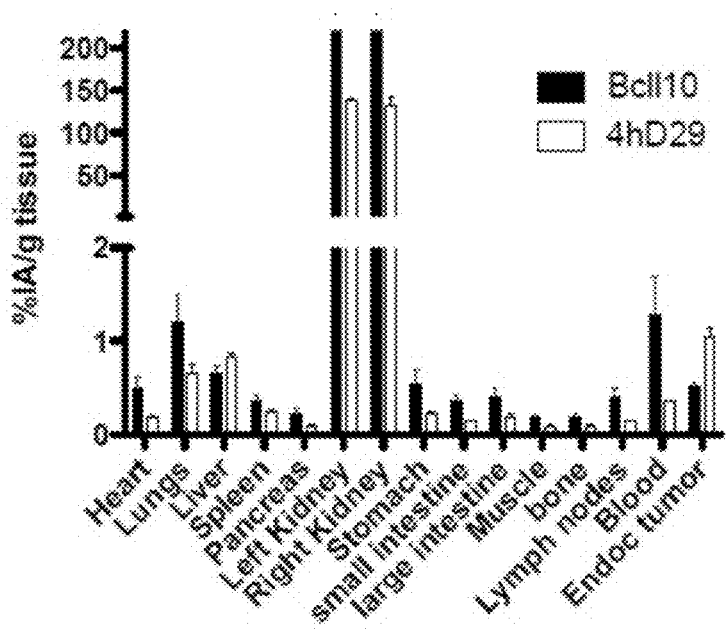
FIGS. 15A-15B—FIG. 15A: % IA/g dissected tissue 1.5 h i.v. injection $^{99m}$Tc-labelled 4hD29 and control (anti Bcl-10) nanobody.
Figure 15B:
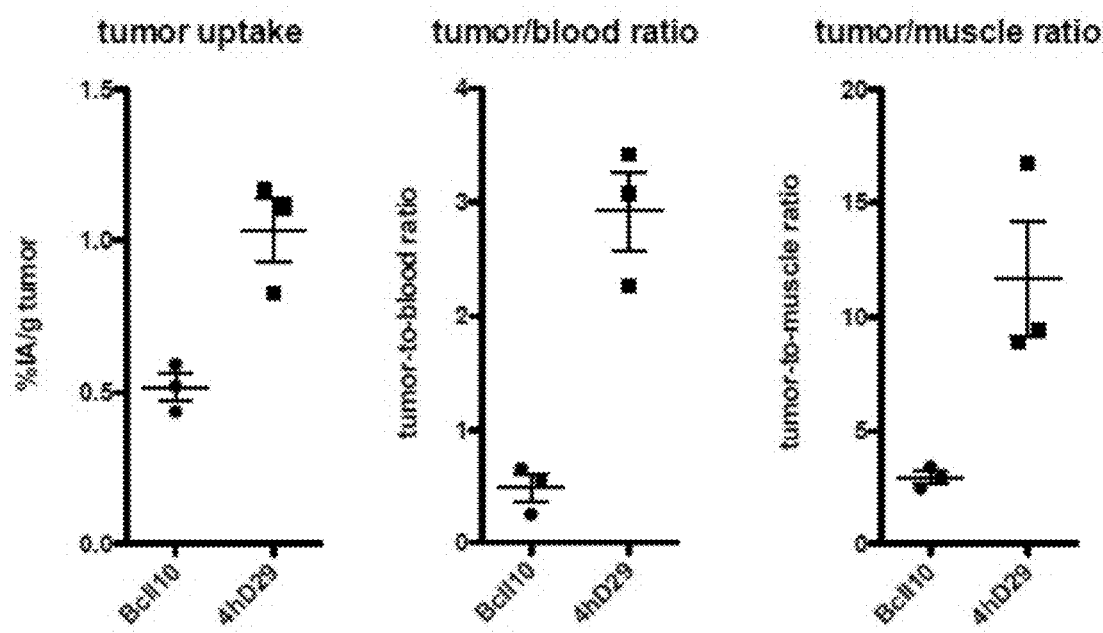

Finally, Endoc cells were grown in rings implanted subcutaneously in mice. Mice were injected i.v. with $^{99m}$Tc-labeled Nb 4hD29 or ctrl Nb and imaged 1 h (not shown) or 3 h p.i. Shown are the quantifications of the signals (n=2). These data clearly show that 4hD29 Nb accumulates in the Endoc graft, but not in the control ring. Ctrl Nb does not accumulate in either of them (FIG. 14).

REFERENCES

1. Del Guerra S, Lupi R, Marselli L, Masini M, Bugliani M, Sbrana S, Torri S, Pollera M, Boggi U, Mosca F, Del Prato S, Marchetti P: Functional and Molecular Defects of Pancreatic Islets in Human Type 2 Diabetes. Diabetes 2005; 54:727-735

2. Ravassard P, Hazhouz Y, Pechberty S, Bricout-Neveu E, Armanet M, Czernichow P, Scharfmann R: A genetically engineered human pancreatic beta cell line exhibiting glucose-inducible insulin secretion. J Clin Invest 2011; 121: 3589-3597

3. Brozzi F, Gerlo S, Grieco F A, Nardelli T R, Lievens S, Gysemans C, Marselli L, Marchetti P, Mathieu C, Tavernier J, Eizirik D L: A Combined "Omics" Approach Identifies N-Myc Interactor as a Novel Cytokine-induced Regulator of IRE1α Protein and c-Jun N-terminal Kinase in Pancreatic Beta Cells. Journal of Biological Chemistry 2014; 289:20677-20693

4. Eizirik D L, Sammeth M, Bouckenooghe T, Bottu G, Sisino G, Igoillo-Esteve M, Ortis F, Santin I, Colli M L, Barthson J, Bouwens L, Hughes L, Gregory L, Lunter G, Marselli L, Marchetti P, McCarthy M I, Cnop M: The human pancreatic islet transcriptome: expression of candidate genes for type 1 diabetes and the impact of pro-inflammatory cytokines. PLoS genetics 2012; 8:e1002552

5. Cardozo A K, Ortis F, Storling J, Feng Y-M, Rasschaert J, Tonnesen M, Van Eylen F, Mandrup-Poulsen T, Herchuelz A, Eizirik D L: Cytokines Downregulate the Sarcoendoplasmic Reticulum Pump Ca2+ ATPase 2b and Deplete Endoplasmic Reticulum Ca2+, Leading to Induction of Endoplasmic Reticulum Stress in Pancreatic β-Cells. Diabetes 2005; 54:452-461

6. Marroqui L, Masini M, Merino B, Grieco F A, Millard I, Dubois C, Quesada I, Marchetti P, Cnop M, Eizirik D L: Pancreatic α Cells are Resistant to Metabolic Stress-induced Apoptosis in Type 2 Diabetes. EBioMedicine 2015; 2:378-385

7. Capito C, Simon M-T, Aiello V, Clark A, Aigrain Y, Ravassard P, Scharfmann R: Mouse Muscle As an Ectopic Permissive Site for Human Pancreatic Development. Diabetes 2013; 62:3479-3487

8. Fridman R, Benton G, Aranoutova I, Kleinman H K, Bonfil R D: Increased initiation and growth of tumor cell lines, cancer stem cells and biopsy material in mice using basement membrane matrix protein (Cultrex or Matrigel) co-injection. Nat Protocols 2012; 7:1138-1144

9. Notta F, Doulatov S, Dick J E: Engraftment of human hematopoietic stem cells is more efficient in female NOD/SCID/IL-2Rgc-null recipients. Blood 2010; 115:3704-3707

10. Shultz L D, Ishikawa F, Greiner D L: Humanized mice in translational biomedical research. Nat Rev Immunol 2007; 7:118-130

11. Farrell C M, O'Leary N A, Harte R A, Loveland J E, Wilming L G, Wallin C, Diekhans M, Barrell D, Searle S M J, Aken B, Hiatt S M, Frankish A, Suner M-M, Rajput B, Steward C A, Brown G R, Bennett R, Murphy M, Wu W, Kay M P, Hart J, Rajan J, Weber J, Snow C, Riddick L D, Hunt T, Webb D, Thomas M, Tamez P, Rangwala S H, McGarvey K M, Pujar S, Shkeda A, Mudge J M, Gonzalez J M, Gilbert J G R, Trevanion S J, Baertsch R, Harrow J L, Hubbard T, Ostell J M, Haussler D, Pruitt K D: Current status and new features of the Consensus Coding Sequence database. Nucleic Acids Research 2014; 42:D865-D872.

The invention claimed is:

1. A binding molecule that specifically binds to the dipeptidyl peptidase VI protein K variant (DPP6-K), wherein said DPP6-K is defined by the amino acid sequence of SEQ ID NO: 1 and wherein said binding molecule is a single domain antibody comprising a complementarity determining region 1 (CDR1) defined by the amino acid sequence of SEQ ID NO 9, a complementary determining region 2 (CDR2) defined by the amino acid sequence of SEQ ID NO 10, and a complementary determining region 3 (CDR3) defined by the amino acid sequence of SEQ ID NO 11.

2. The binding molecule according to claim 1, wherein the binding molecule is labelled with a radioisotope, a fluorescent moiety, a chemiluminescent moiety, a bioluminescent moiety, a chemifluorescent moiety, or a metal or magnetic moiety for visualising or measuring pancreatic beta-cell mass.

3. The binding molecule according to claim 1, wherein the binding molecule comprises a heavy chain variable domain defined by the amino acid sequence of SEQ ID No 8.

4. A method for detecting beta-cell mass, comprising the steps of:
   a) labelling beta cells in a sample of a subject based on the presence of DPP6-K using the binding molecule of claim 2; and
   b) detecting or visualizing the labelled beta cells.

5. A method for measuring pancreatic beta-cell mass, the method comprising the steps of:
   a) detecting or visualizing the beta cells in a sample of a subject using the method according to claim 4; and
   b) quantifying the amount of labelled beta cells.

6. A method of diagnosing a beta-cell-related disorder in a subject, the method comprising the steps of:
   a) introducing the labelled binding molecule of claim 2 into the subject;
   b) visualizing the labelled binding molecule specifically located to the beta-cell population in the subject in vivo;
   c) quantifying the beta-cell mass in said subject;
   d) comparing the beta-cell mass data obtained in step c) with a beta-cell mass of a healthy subject or of a previous analysis of the subject;
   e) diagnosing the subject as having diabetes or being at risk of having diabetes when the level of beta-cell mass obtained in step c) is reduced as compared to that of the healthy subject; and
   f) diagnosing the subject as having hyperinsulinemia or being at risk of having hyperinsulinemia when the level of beta-cell mass obtained in step c) is increased as compared to that of the healthy subject or of the previous analysis of the subject.

7. The method according to claim 6, wherein said in vivo visualisation is done using a PET, PET-CT, SPECT, or Mill scan, or through fluorescent imaging.

8. The method of claim 6, wherein the beta-cell-related disorder is type 1 diabetes mellitus, type 2 diabetes mellitus, hyperinsulinemia, obesity, or occurrence of insulinoma.

9. A method for determining the success of a transplantation of beta cells in a subject, the method comprising the steps of:
   a) measuring the amount of beta-cell mass in the subject at one or more time points after transplantation of the subject with beta cells with the method according to claim 4; and b) determining the success of the transplantation by comparing the beta-cell mass over time and evaluating the evolution of beta-cell mass over time.

10. A method for purifying pancreatic beta cells from pancreatic non-beta cells, the method comprising the steps of:
    a) tagging the pancreatic beta cells with the labelled binding molecule of claim 2 to form labelled pancreatic beta cells; and
    b) isolating the labelled pancreatic beta cells from the pancreatic non-beta cells through the labelled binding molecule on the labelled pancreatic beta cells, thereby obtaining a substantially pure beta-cell preparation.

11. A method for identifying a regeneration of beta cells, the method comprising the steps of:
    a) tagging the beta cells with the binding molecule of claim 1 to form labelled beta cells;
    b) isolating the labelled beta cells from non-labelled cells through the labelled binding molecule on the labelled beta cells, thereby obtaining a substantially pure regenerated beta-cell preparation; and
    c) performing immunohistochemistry to identify the number of regenerated beta cells and define the mass of the regenerated beta cell.

12. A method for identifying stem cell populations treated to differentiate towards functional insulin-expressing beta stem cells, the method comprising the steps of:
    a) tagging the treated stem cells with the labelled binding molecule of claim 2 to form labelled treated stem cells; and
    b) isolating the labelled treated stem cells from non-labelled cells through the labelled binding molecule on the labelled treated stem cells, thereby obtaining a substantially pure beta stem cell preparation.

13. A method for treating diabetes in a subject suffering therefrom, the method comprising delivering a therapeutic agent specifically to beta cells of the subject with a binding molecule according to claim 1.

14. A kit comprising the binding molecule of claim 1.

15. A method for diagnosing type 1 diabetes (T1D) in a subject, the method comprising:
    administering the binding molecule of claim 1 to the subject; and
    diagnosing the subject as having T1D or an increased risk of T1D based on the detection of beta cells or beta-cell debris in the circulation of the subject.

16. A method for monitoring beta cell transplants in a subject having undergone beta cell transplantation, the method comprising:
    administering to the subject the labelled binding molecule of claim 2; and
    imaging the subject, thereby monitoring the beta cell transplant in the subject.

17. A method for treating a beta-cell related disorder in a subject, the method comprising:
    a) introducing the labelled binding molecule of claim 2 into a subject;
    b) quantifying the beta-cell mass in said subject;
    c) comparing the beta-cell mass data obtained in step c) with a beta-cell mass data of a healthy subject or of a previous analysis of the subject; and
    d) treating the subject for diabetes if the amount of the subject beta cell mass in step c) is reduced compared to that of the healthy subject; or
    e) treating the subject for hyperinsulinemia if the subject beta cell mass in step c) is increased compared to that of the healthy subject or of the previous analysis of the subject.

* * * * *

UNITED STATES PATENT AND TRADEMARK OFFICE
CERTIFICATE OF CORRECTION

Page 1 of 1

PATENT NO. : 11,243,214 B2
APPLICATION NO. : 16/092212
DATED : February 8, 2022
INVENTOR(S) : Eizirik Decio Laks et al.

It is certified that error appears in the above-identified patent and that said Letters Patent is hereby corrected as shown below:

In the Claims

Column 56, Line 56, Claim 7, delete "or Mill" and insert --or MRI--.

Column 57, Line 17, Claim 11, delete "claim 1" and insert --claim 2--.

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*